US008950256B2

(12) United States Patent
Kautz et al.

(10) Patent No.: US 8,950,256 B2
(45) Date of Patent: *Feb. 10, 2015

(54) DYNAMIC FIT UNIT

(71) Applicant: Dorel Hungary KFT Luxembourg Branch, Luxembourg (LU)

(72) Inventors: Christopher Kautz, Danbury, CT (US); Scott Alan Rice, San Diego, CA (US); Jean-Paul Racine, Chambly (CA); Jason Andrew Clark, Southbury, CT (US); Antonio Giannascoli, St. Laurent (CA)

(73) Assignee: Dorel Hungary KFT Luxembourg Branch, Luxembourg (LU)

( * ) Notice: Subject to any disclaimer, the term of this patent is extended or adjusted under 35 U.S.C. 154(b) by 288 days.

This patent is subject to a terminal disclaimer.

(21) Appl. No.: 13/622,008

(22) Filed: Sep. 18, 2012

(65) Prior Publication Data

US 2013/0065733 A1    Mar. 14, 2013

Related U.S. Application Data

(63) Continuation-in-part of application No. 13/019,369, filed on Feb. 2, 2011, which is a continuation of application No. 11/845,986, filed on Aug. 28, 2007, now Pat. No. 7,905,817.

(60) Provisional application No. 60/823,777, filed on Aug. 29, 2006, provisional application No. 60/868,433, filed on Dec. 4, 2006.

(51) Int. Cl.
*A61B 5/22* (2006.01)
*A63B 22/06* (2006.01)
(Continued)

(52) U.S. Cl.
CPC .............. *A63B 22/0605* (2013.01); *A63B 69/16* (2013.01); *G06F 19/3481* (2013.01);
(Continued)

(58) Field of Classification Search
USPC .................. 73/379.01; 482/57, 51, 52, 61
See application file for complete search history.

(56) References Cited

U.S. PATENT DOCUMENTS 3,062,204 A    11/1962   Stefano
3,750,479 A     8/1973   Gause et al.
(Continued)

FOREIGN PATENT DOCUMENTS

CA    2599244 A1    2/2008
EP    1410984 A1    4/2004
(Continued)

OTHER PUBLICATIONS

International Search Report in PCT/US2013/059162, mailed Dec. 18, 2013.

*Primary Examiner* — Jewel V Thompson
(74) *Attorney, Agent, or Firm* — Brian G. Gilpin; Godfrey & Kahn, S.C.

(57) ABSTRACT

An optimal bicycle frame size based on operational characteristics provided by a rider when riding a dynamic fit unit is determined. A best-fit bicycle frame size that is a closest match to the optimal frame size is determined. At least one of the optimal X,Y location of the bicycle's handlebar relative to the bottom bracket, and the optimal X,Y location of the bicycle's seat relative to the bottom bracket, is determined. A stem and spacer from a list of available stems and spacers that will best fit between the head tube of the best-fit frame and the optimal X,Y location of the handlebar is determined. A seat post from a list of available seat posts that will best fit between the seat tube of the best-fit frame and the optimal X,Y location of the seat is determined. A list of the best-fit frame, the best fit stem and spacer, and the best fit seat post, is produced.

18 Claims, 22 Drawing Sheets

(51) Int. Cl.
   *A63B 69/16*   (2006.01)
   *G06F 19/00*   (2011.01)
   *B62K 3/00*    (2006.01)

(52) U.S. Cl.
   CPC .............. *B62K 3/00* (2013.01); *A63B 2220/17* (2013.01); *A63B 2220/34* (2013.01); *A63B 2220/51* (2013.01); *A63B 2220/54* (2013.01); *A63B 2225/09* (2013.01); *A63B 2225/096* (2013.01); *A63B 2225/20* (2013.01); *A63B 2230/06* (2013.01)
   USPC ..................................................... 73/379.01

(56) References Cited

U.S. PATENT DOCUMENTS

| | | | |
|---|---|---|---|
| 4,637,604 A | 1/1987 | DuPont | |
| 4,768,777 A | 9/1988 | Yang | |
| 5,035,418 A | 7/1991 | Harabayashi | |
| 5,158,515 A | 10/1992 | Turcios | |
| 5,240,417 A | 8/1993 | Smithson et al. | |
| 5,312,311 A | 5/1994 | Pearson | |
| 5,527,248 A | 6/1996 | Crivello | |
| 5,549,527 A | 8/1996 | Yu | |
| 5,782,639 A | 7/1998 | Beal | |
| 5,890,995 A | 4/1999 | Bobick et al. | |
| 5,913,752 A | 6/1999 | Bolf | |
| 6,066,073 A | 5/2000 | Stearns et al. | |
| 6,126,577 A | 10/2000 | Chang | |
| 6,159,130 A | 12/2000 | Torvinen | |
| 6,251,047 B1 | 6/2001 | Stearns et al. | |
| 6,648,802 B2 | 11/2003 | Ware | |
| 6,669,603 B1 | 12/2003 | Forcillo | |
| 7,081,070 B1 | 7/2006 | Washington et al. | |
| 7,399,259 B2 | 7/2008 | Somwong | |
| 7,438,672 B1 | 10/2008 | Rylander et al. | |
| 7,481,746 B2 | 1/2009 | Ibarguren | |
| 7,641,600 B2 | 1/2010 | Bingham, Jr. et al. | |
| 7,682,286 B2 * | 3/2010 | Badarneh et al. | 482/5 |
| 7,762,930 B2 | 7/2010 | Egger | |
| 7,771,325 B2 * | 8/2010 | Baker | 482/57 |
| 7,905,817 B2 * | 3/2011 | Giannascoli et al. | 482/57 |
| 2002/0151414 A1 | 10/2002 | Baker | |
| 2003/0171190 A1 | 9/2003 | Rice | |
| 2004/0053750 A1 | 3/2004 | Forcillo | |
| 2004/0176218 A1 | 9/2004 | Fan | |
| 2004/0198561 A1 | 10/2004 | Corbalis et al. | |
| 2004/0237666 A1 | 12/2004 | Winkenbach et al. | |
| 2004/0248702 A1 | 12/2004 | Baker | |
| 2005/0221960 A1 | 10/2005 | Miyamaru et al. | |
| 2005/0221961 A1 | 10/2005 | Forcillo | |
| 2005/0239609 A1 | 10/2005 | Chen | |
| 2006/0003870 A1 | 1/2006 | Corbalis et al. | |
| 2006/0003872 A1 | 1/2006 | Chiles et al. | |
| 2006/0094569 A1 | 5/2006 | Day | |
| 2006/0105887 A1 | 5/2006 | Hao | |
| 2006/0172867 A1 | 8/2006 | Lee | |
| 2006/0199700 A1 | 9/2006 | LaStayo et al. | |
| 2006/0234836 A1 | 10/2006 | Kuo | |
| 2006/0234837 A1 | 10/2006 | Kuo | |
| 2006/0270522 A1 | 11/2006 | Yonehana et al. | |
| 2007/0003910 A1 | 1/2007 | Kirila | |
| 2007/0099766 A1 | 5/2007 | Pyles et al. | |
| 2007/0099767 A1 | 5/2007 | Harashima | |
| 2007/0105694 A1 | 5/2007 | Panatta | |
| 2007/0142177 A1 | 6/2007 | Simms et al. | |
| 2007/0149364 A1 | 6/2007 | Blau et al. | |
| 2007/0161467 A1 | 7/2007 | Lee | |
| 2007/0173381 A1 | 7/2007 | Chen et al. | |
| 2007/0281835 A1 | 12/2007 | Baker | |
| 2008/0058170 A1 | 3/2008 | Giannascoli et al. | |
| 2012/0202653 A1 | 8/2012 | Seastrom | |

FOREIGN PATENT DOCUMENTS

| | | | |
|---|---|---|---|
| EP | 2353983 A1 | 8/2011 | |
| FR | 2495307 A1 | 6/1982 | |
| JP | S5932801 A | 6/1982 | |
| WO | WO2010034078 A1 | 4/2010 | |

* cited by examiner

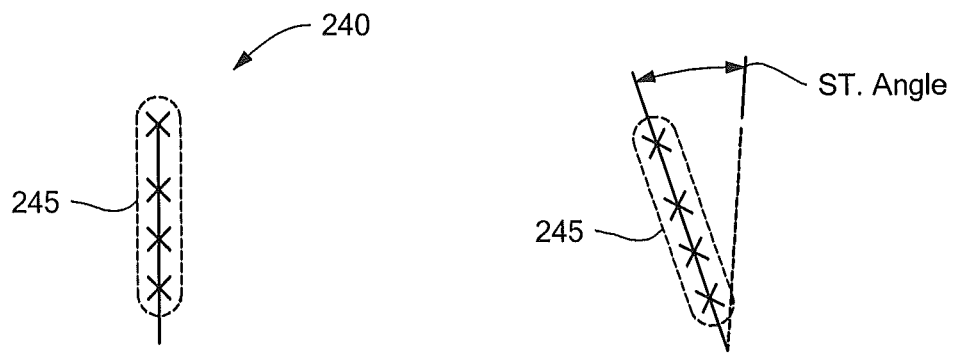
*FIG. 14A*           *FIG. 15A*
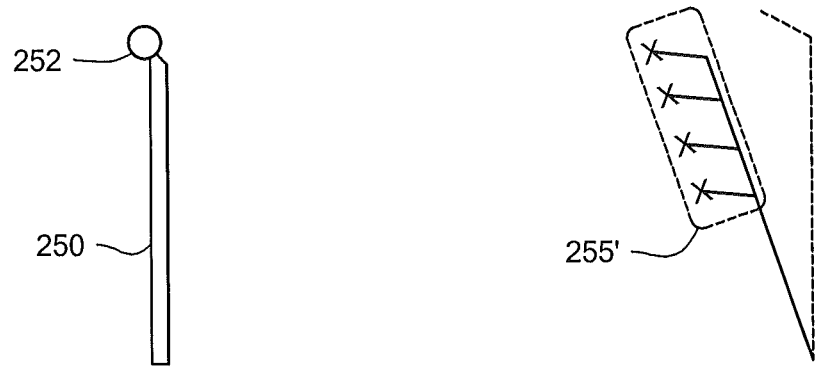
*FIG. 14B*           *FIG. 15B*

DYNAMIC FIT UNIT

CROSS REFERENCE TO RELATED APPLICATIONS

The present patent application is a continuation-in-part of U.S. patent application Ser. No. 13/019,369, filed Feb. 2, 2011, which is a continuation of U.S. patent application Ser. No. 11/845,986, filed on Aug. 28, 2007, which claims priority to U.S. Provisional Patent Applications No. 60/823,777, filed on Aug. 29, 2006, and No. 60/868,433, filed on Dec. 4, 2006, all of which are herein incorporated by reference in their entireties.

FIELD OF THE APPLICATION

The present application relates to stationary bicycles, particularly to an adjustable stationary bicycle as used for exercise, as a fitting apparatus in purchasing a bicycle, and/or as an interface in the gaming industry and, more particularly, to a method of determining a best fit bicycle for a given rider.

BACKGROUND OF THE ART

In riding a bicycle, the pedaling power of the user is a primary factor in determining how fast the rider will get to the destination. There are other factors associated with the bicycle and the interaction between the rider and the bicycle, such as the wind resistance (i.e., drag coefficient) and the weight of the rider and/or bicycle.

In order to optimize the power output of the rider on the bicycle, it is important that the bicycle be of appropriate dimensions for the rider. The rider must be in an aerodynamic riding position as much as possible, but the position should affect the breathing and the pedaling of the rider as little as possible. The pedaling power is directly related to the heart rate of the rider, whereby adequate breathing is essential to an optimized riding position.

At present, when purchasing a bicycle, a rider moves onto the bike having its rear wheel supported by a trainer. According to the salesman's experience, various adjustments are made (vertical and horizontal position of the seat, stem length and handlebar height) until a suitable riding position is reached, often as visually decided by the salesman. The rider must at the very least stop pedaling and lean forward to make adjustments to the seat. In some instances, the rider must come off the bicycle for adjustments to be made.

In the indoor training industry and more specifically in gyms, stationary bikes are often limited as to the adjustable parameters that are available for the user. Moreover, a user of the stationary bicycle often lacks the ability or the assistance of a trainer to adjust the bicycle to a proper fit. Therefore, a rider training on a stationary bicycle often does not sit in the optimized riding position, therefore not fully benefiting from the workout.

SUMMARY OF THE APPLICATION

An embodiment of the invention includes a dynamic fit unit having a frame, a crankset rotatably mounted to the frame at a bottom bracket, a handlebar adjustably disposed on the frame to be adjustable in X and Y directions relative to the crankset, a seat adjustably disposed on the frame to be adjustable in X and Y directions relative to the crankset, a mechanism operably connected to the handlebar and the seat to facilitate adjustment of the respective handlebar and seat in the X and Y directions, and a bicycle controller system having a bicycle controller responsive to computer executable code. The bicycle controller system facilitates: movement of the handlebar and the seat in the X and Y directions; determination of an optimal bicycle frame size for a rider based on operational characteristics provided by the rider when riding the dynamic fit unit; determination of a best-fit bicycle frame size that is a closest match to the optimal frame size based on a comparison of available frame sizes stored in a database, the best-fit bicycle frame having a head tube and a seat tube; determination of at least one of the optimal X,Y location of the handlebar relative to the bottom bracket based on the location of the rider's hands, and the optimal X,Y location of the seat relative to the bottom bracket based on the location of the rider's derriere; determination of a stem and spacer from a list of available stems and spacers that will best fit between the head tube of the best-fit frame and the optimal X,Y location of the handlebar; determination of a seat post from a list of available seat posts that will best fit between the seat tube of the best-fit frame and the optimal X,Y location of the seat; and, output of a list of the best-fit frame, the best fit stem and spacer, and the best fit seat post.

An embodiment of the invention includes a method for use with a dynamic fit unit. An optimal bicycle frame size for a rider based on operational characteristics provided by the rider when riding the dynamic fit unit is determined. A best-fit bicycle frame size that is a closest match to the optimal frame size based on a comparison of available frame sizes stored in a database, the best-fit bicycle frame having a head tube and a seat tube, is determined. At least one of the optimal X,Y location of the handlebar relative to the bottom bracket based on the location of the rider's hands, and the optimal X,Y location of the seat relative to the bottom bracket based on the location of the rider's derriere, is determined. A stem and spacer from a list of available stems and spacers that will best fit between the head tube of the best-fit frame and the optimal X,Y location of the handlebar is determined. A seat post from a list of available seat posts that will best fit between the seat tube of the best-fit frame and the optimal X,Y location of the seat is determined. A list of the best-fit frame, the best fit stem and spacer, and the best fit seat post, is produced.

BRIEF DESCRIPTION OF THE DRAWINGS

FIG. 14A depicts a one-line diagram representation of the available seat posts overlaid on top of each other, where the X's depict a third cloud of points representative of the location of where a seat would attach to the end of a respective seat post, in accordance with an embodiment of the invention;

FIG. 14B depicts an alternative seat post for use in accordance with an embodiment of the invention;

FIG. 15A depicts the third cloud of points from FIG. 14 rotated to the angle of the seat tube (ST Angle) of the best fit frame from FIG. 9, in accordance with an embodiment of the invention;

FIG. 15B depicts an alternative third cloud of points similar to those of FIG. 15A but associated with the seat post of FIG. 14B;

FIG. 18 depicts a third screen image, in accordance with an embodiment of the invention;

FIG. 19 depicts a fourth screen image, in accordance with an embodiment of the invention;

DESCRIPTION OF THE INVENTION

Figure 1:
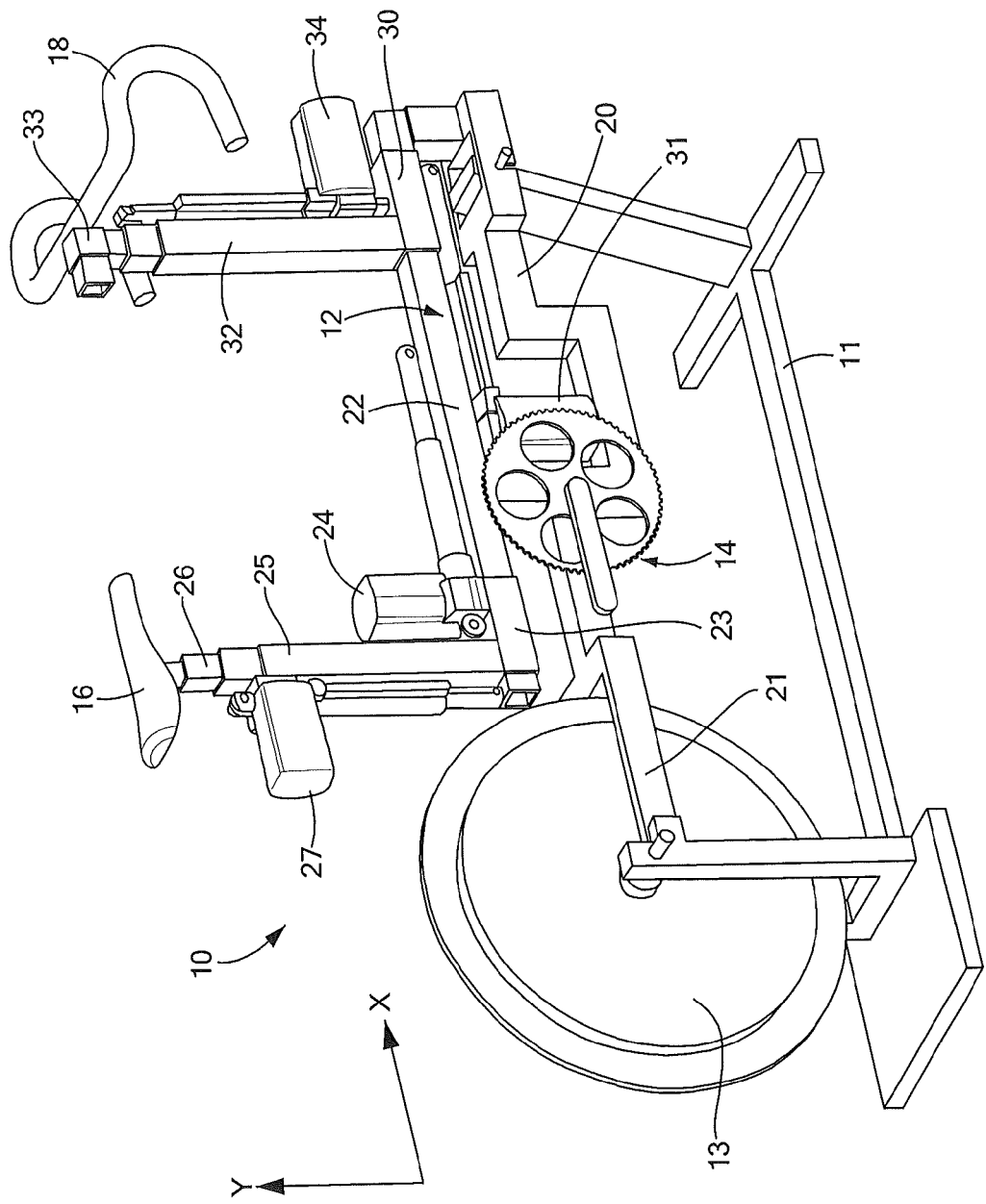
FIG. 1 is a rear perspective view of an adjustable stationary bicycle in accordance with an embodiment of the invention.
Figure 2:
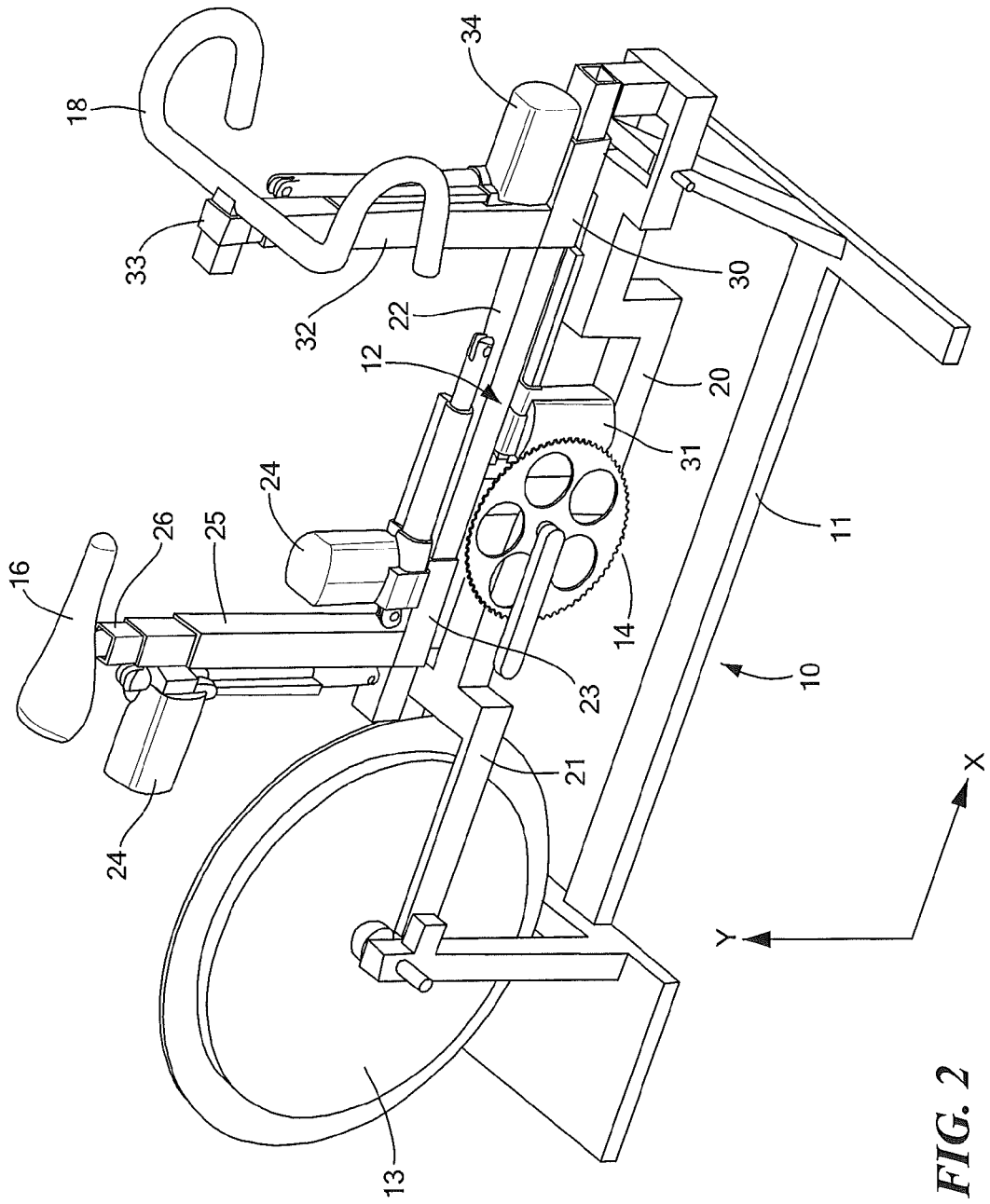
FIG. 2 is a front perspective view of the adjustable stationary bicycle of FIG. 1.
Figure 3:
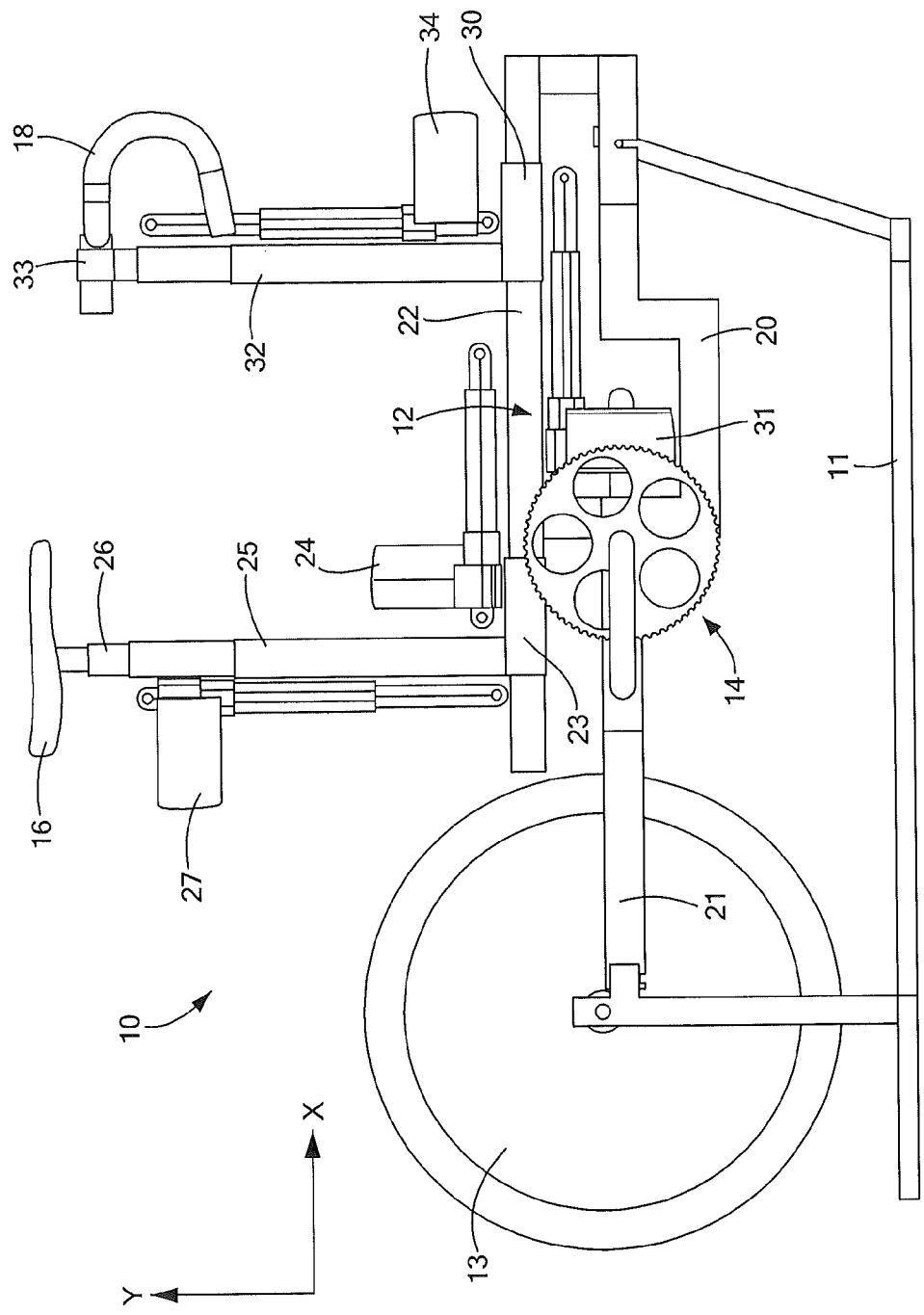
FIG. 3 is a side elevation view of the adjustable stationary bicycle of FIG. 1.

Referring now to the drawings and more particularly to FIGS. 1 to 3, an adjustable stationary bicycle in accordance with a first embodiment is generally shown at 10. The stationary bicycle 10, also herein referred to as a Dynamic Fit Unit (DFU), has a base 11, a frame 12, an exercise wheel 13, a crankset 14, a seat 16 and a handlebar 18.

The base 11 supports a remainder of the bicycle 10. The base 11 is for instance mounted on the floor.

A frame 12 is connected to the base 11. The frame supports the various user interface components of the bicycle 10, namely the crankset 14, the seat 16 and the handlebar 18.

The exercise wheel 13 is related to the crankset 14. The power output of the user of the bicycle 10 is typically measured using the exercise wheel 13. The exercise wheel 13 is also actuated to control the resistance to pedaling.

The crankset 14 has pedals (not shown) and receives the pedaling actuation from the user of the bicycle 10. The pivot axis of the crankset 14 relates to the pivot axis of a crankset of a bicycle pivotally disposed within a bottom bracket of the bicycle frame.

The seat 16 supports the user of the bicycle 10 in a riding position.

The handlebar 18 is provided as a support for the arms of the user.

The frame 12 has a support beam 20 by which it is connected to the base 11. The support beam 20 has a chainstay between which the exercise wheel 13 is in a rotational relation. Although not shown, a chain/chainring and gears, belt/pulleys or similar transmissions are provided between the wheel 13 and the crankset 14 for the transmission of the pedaling power of the user to the wheel 13.

A rail 22 is supported by the support beam 20. In an embodiment, the rail 22 is generally parallel to the ground. A carriage 23 is slidingly mounted onto the support beam 20, so as to form a prismatic joint therewith (i.e., translational one-DOF joint). As it is supported by the carriage 23, the seat 16 is displaceable in translation along the X-axis. The prismatic joint formed by the rail 22 and the carriage 23 is actuated by actuator 24.

A seat tube 25 is connected to the carriage 23 and in an embodiment is in a perpendicular relation therewith. A seat post support 26 is telescopically engaged into the seat tube 25, so as to form another prismatic joint. As the seat post of the seat 16 is locked to the seat post support 26, the seat is displaceable in translation along the Y-axis. The prismatic joint formed by the seat tube 25 and the seat post support 26 is actuated by actuator 27.

The handlebar 18 is also displaceable in translation along the X-axis and the Y-axis. More specifically, a carriage 30 supporting the handlebar 18 is operatively mounted to a front end of the rail 22, thereby forming a prismatic joint. The direction of the carriage 30 is along the X-axis. In the illustrated embodiment, the displacement of the handlebar 18 along the X-axis is actuated by actuator 31.

A head tube 32 is mounted to the carriage 30, and in an embodiment is in a perpendicular relation therewith. A bracket 33 is telescopically inserted into the head tube 32 so as to form a prismatic joint displaceable along the Y-axis direction. Actuator 34 powers the prismatic joint along the Y-axis direction.

Although the actuators 24, 27, 31 and 34 are preferably electrically powered linear actuators, it is contemplated to use either stepper motors or manual actuation as well. The translational degrees of freedom of the seat 16 and of the handlebar 18 are mechanically controlled and self-supported/self-locked such that actuation is required to displace the seat 16 and/or handlebar 18. In the illustrated embodiments, the seat 16 and handlebar 18 are therefore fixed into X and Y positions, and can only be displaced by actuation of the prismatic joints. Therefore, the seat 16 and the handlebar 18 are displaceable even while a rider is supported in a riding position.

The bracket 33 is a quick-release mechanism allowing different handlebars 18 to be mounted rapidly onto the stationary bicycle 10. Alternatively, a handlebar extendable in a Z-axis (perpendicular to both the X- and Y-axes according to an orthogonal set of X-Y-Z axes) is considered.

Although not shown, the crankset 14 is preferably of the extendable type, in that the cranks can be adjusted to different lengths. One contemplated crankset system has the cranks pivotally off-center from the chainring, so as to be adjustable to different crank lengths.

Various sensors are provided in order to measure the performance of the rider on the stationary bicycle 10. For instance, referring to FIG. 5, a power sensor 40 and a cadence sensor 41 are respectively provided in association with the exercise wheel 13 and the crankset 14 to measure the pedaling power and the cadence of a rider. Other configurations for these sensors, and for other sensors 42, are considered, such as a heart-rate monitor, pressure sensors for the pedals, etc.

Figure 4:
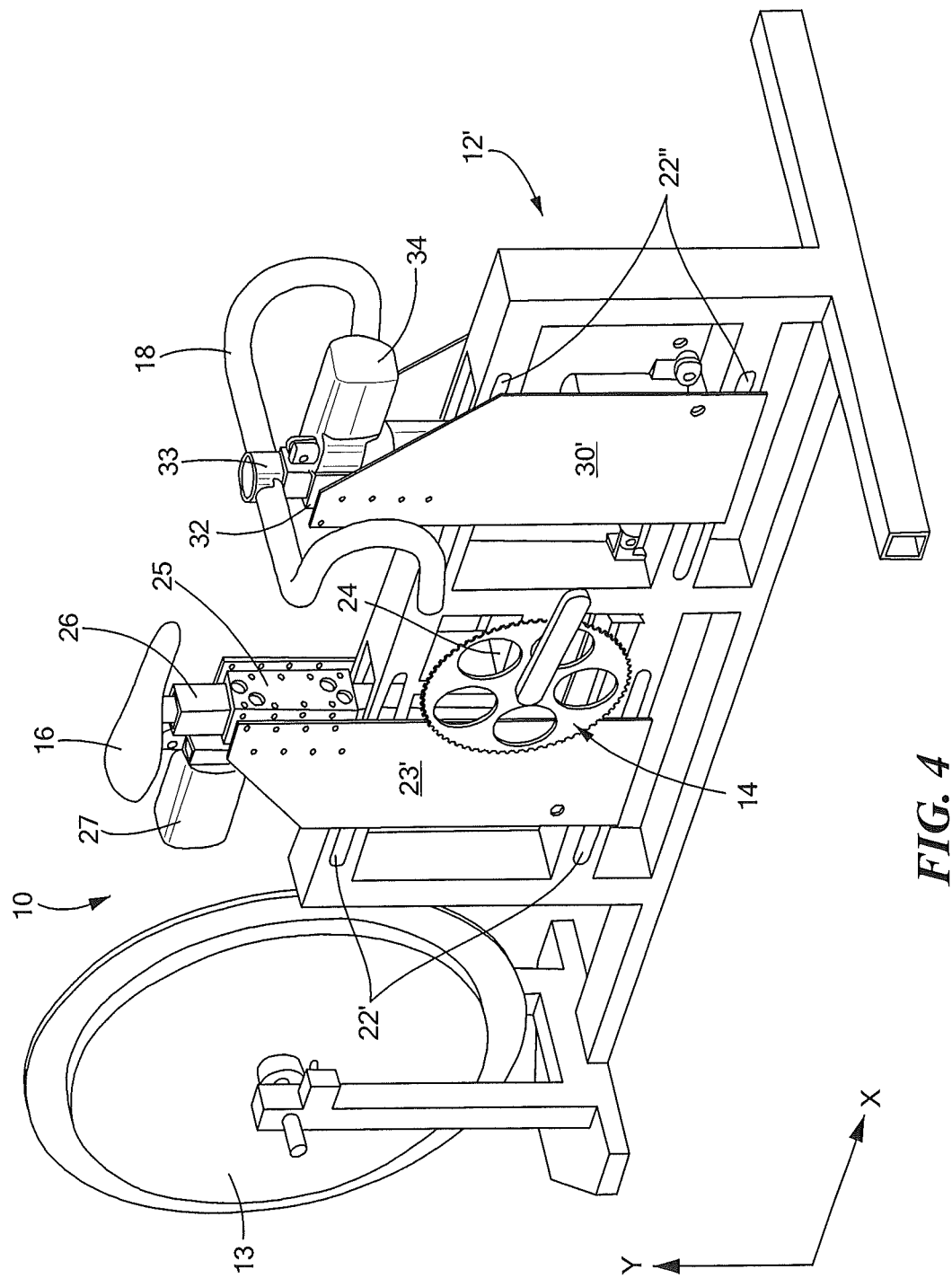
FIG. 4 is a front perspective view of an adjustable stationary bicycle in accordance with another embodiment of the invention.

It is considered to have the stationary bicycle 10 take different configurations to enhance its stiffness. Referring to FIG. 4, an alternative embodiment of the stationary bicycle is also illustrated as 10, but features a frame 12' that is different than the frame 12 of the stationary bicycle of FIGS. 1 to 3. Many components are similar between the stationary bicycles 10 of FIGS. 1-3 and of FIG. 4, whereby like parts will bear like reference numerals.

The frame 12' has a pair of guideways 22' supporting the carriage 23', such that the carriage 23' is displaceable in translation along the X-axis, enabling the horizontal adjustment of the seat 16. The carriage 23' consists of a pair of parallel plates that support the seat tube 25.

Similarly, the frame 12' has a pair of guideways 22" supporting the carriage 30', such that the carriage 30' is displaceable in translation along the X-axis, further enabling the horizontal adjustment of the seat 16. The carriage 30' consists of a pair of parallel plates that support the head tube 32.

The configuration of the frame 12' (FIG. 4), although similar in construction to the frame 12 (FIGS. 1-3), provides added structural rigidity to the stationary bicycle 10. Alternative frame configurations are considered as well.

Figure 5:
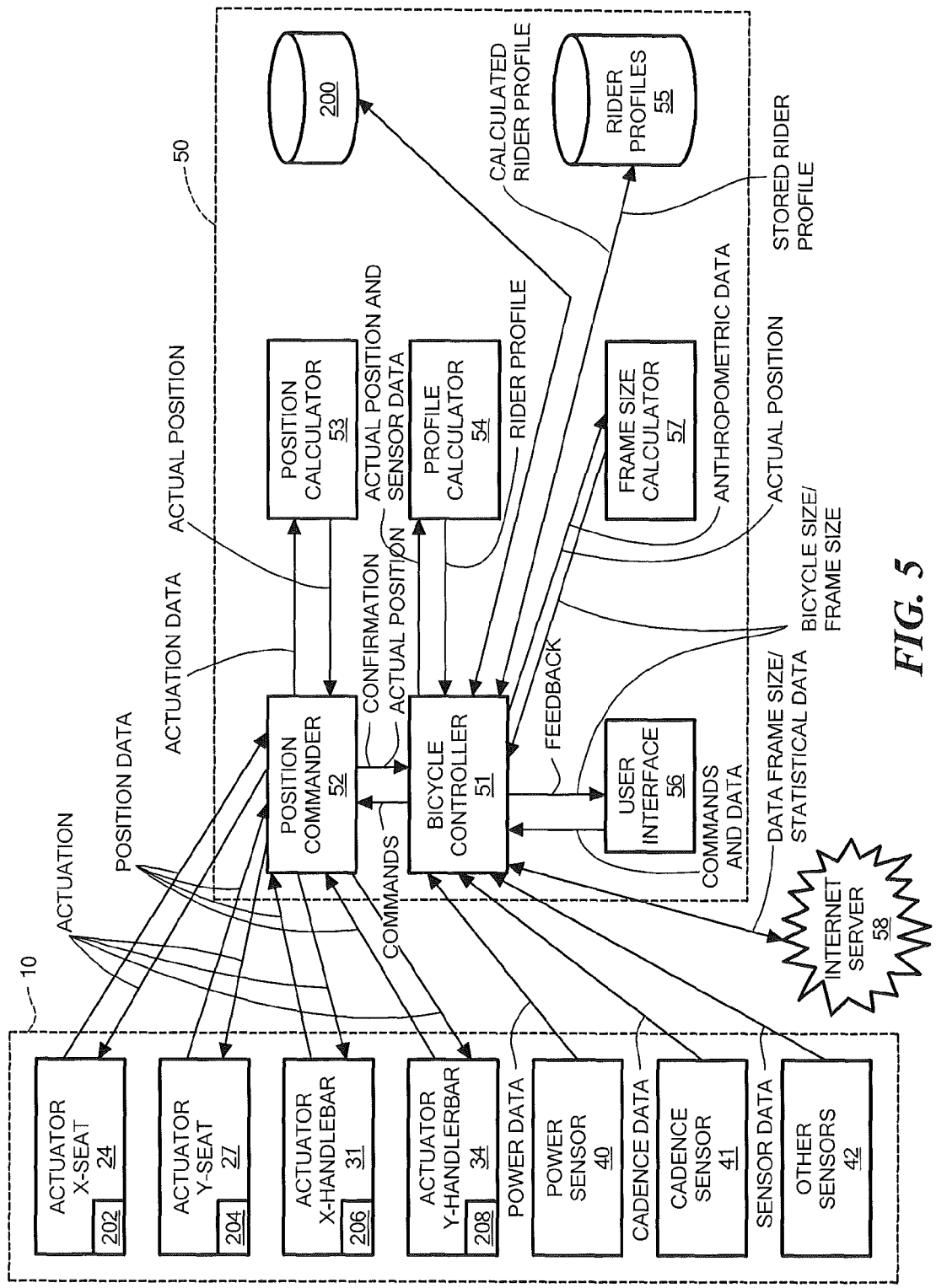
FIG. 5 is a block diagram of a bicycle controller system used in combination with the adjustable stationary bicycle of FIGS. 1 and 4.

Referring to FIG. 5, a stationary bicycle controller system in accordance with an embodiment is generally shown at 50. The bicycle controller system 50 is in communication with the actuators 24, 27, 31 and 34, as well as with the sensors 40, 41 and 42.

The bicycle controller system 50 has a bicycle controller 51 that is a processing unit (PC, microprocessor, or the like). The bicycle controller 51 receives data from the power sensor 40, the cadence sensor 41 and the other sensors 42.

A position commander 52 is connected to the bicycle controller 51, and is in association with the actuators 24, 27, 31 and 34. More specifically, the actuation of the actuators 24, 27, 31 and 34 is controlled by the commander 52. A position calculator 53 is connected to the position commander 52 and determines the position of the seat 16 and the handlebar 18 in the X-Y coordinate system illustrated in FIGS. 1 to 3.

As an example, a reference point for the X and Y coordinates of the seat 16 and the handlebar 18 is a center of the crankset 14, which correlates with the center of the bottom bracket of a bicycle frame. Considering that the feet of the rider are locked to the cranks of the crankset 14, the center of the crankset 14 constitutes a fixed point well suited to be used as a reference for the position of the seat 16 and the handlebar 18.

The position calculator 53 may operate in different ways. For instance, in an embodiment a calibration is performed every time the stationary bicycle 10 is turned on, so as to relate the degree of actuation of the actuators 24, 27, 31 and 34 to X and Y positions relative to the reference. In an embodiment, the actuators 24, 27, 31 and 34 are subjected to a homing movement (moved to a null extension) to be calibrated. Alternatively, sensors 202, 204, 206, 208 (see FIG. 5) may be provided in the actuators 24, 27, 31 and 34, or on the various prismatic joints, so as to detect the XY positions of the seat 16 and the handlebar 18 with respect to the reference. The use of sensors is considered for manually actuated mechanisms of displacements for the seat 16 and the handlebar 18.

A profile calculator 54 is connected to the bicycle controller 51. The profile calculator 54 receives the various data from the sensors 40-42, as well as the X and Y positions of the seat 16 and the handlebar 18, as a function of time. Accordingly, the performance of the rider (pedaling power, cadence, heart rate, for example) is related to the dimensions of the stationary bicycle 10. All information is related to rider identification and characteristics (e.g., name, anthropometric measurements, weight, age, etc.) in the form of a rider profile in a rider profile database 55. Additional information can be recorded under the rider profile, such as the preferred dimensions of the stationary bicycle 10.

A user interface 56 is connected to the bicycle controller 51. The user interface 56 is typically a monitor with touch keys or a keyboard, through which the user interface 56 is commanded and information is entered (e.g., rider identification). In an embodiment, the user interface 56 displays actuator controls, for the manual control of the actuation of the actuators 24, 27, 31 and 34. It is considered to provide a touch-screen with icons represent available directions of displacement for the seat 16 and the handlebar 18.

The user interface 56 may include other peripherals, such as a printer, ports for plug-in devices (e.g., USB port), digital camera, etc. Smart cards and chip cards can be used to store the rider profile.

Amongst the various applications considered, the use of the stationary bicycle 10 as a training device in a public gym setting is contemplated. When a rider wants to use the bicycle 10, his/her identification is entered into the bicycle controller system 50, whereby the rider profile is retrieved from the database 55. The bicycle controller 51 transmits the information to the position commander 52 such that the size of the stationary bicycle 10 is adjusted as a function of the rider identification.

For a new user of the stationary bicycle 10, a rider profile is created and saved in the rider profile database 55. It is considered to provide statistical data relating anthropometric data of users to desired bicycle dimensions. Accordingly, by entering anthropometric data pertaining to a user, the bicycle controller 51 can select a suitable bicycle size as a function of the anthropometric data. As described hereinafter, a frame size calculator 57 is used to select a suitable bicycle size from the anthropometric data. Alternatively, from statistical data, formulas can be derived to determine initial bicycle dimensions as a function of anthropometric data. In an embodiment discussed below in connection with method 500 (FIG. 9), the functionality of frame size calculator 57 is expanded to include determination of a best fit bicycle frame, stem, spacer(s), and seat post. Further additional functionality of frame size calculator 57 discussed below includes determination of riding apparel suitable for the person/rider being fitted. As such, the term "frame size calculator" could be replaced with the term "custom calculator", and still be consistent with the description of the invention described herein.

Moreover, the rider profile may include the performance of the rider at different bicycle dimensions. Therefore, an optimal bicycle size can be determined from the review of the information gathered in the database 55 following calculations by the profile calculator 54. This is particularly useful for elite athletes. Alternatively, a trainer can assist the rider in trying different bicycle sizes, to then enter the dimensions, at a position selected by the trainer or the rider.

As another application, the stationary bicycle 10 is used as a fitting apparatus to determine an optimal bicycle size. The stationary bicycle 10 is used with the controller system 50 to gather performance information associated with bicycle size. The use of actuators 24, 27, 31 and/or 34 enables a dynamic fitting. More specifically, the controller system 50 may direct a plurality of incremental changes to have the rider try various adjusted positions while not interrupting his/her pedaling. As an alternative, the rider profile data from the database 55 may then be interpreted to identify the optimal position. With the rider profile, the optimal bicycle size (according to the type of bicycle, such as road bike, mountain bike, cyclo-cross bike, etc.) for the rider can be determined.

When the stationary bicycle 10 is used as part of a fitting apparatus, it is considered to provide the controller system 50 with the frame size calculator 57. The frame size calculator 57 receives the actual position data from the bicycle controller 51 (i.e., the adjusted position following testing by the user), and produces frame size data. The frame size calculator 57 is also provided to identify initial seat and handlebar positions from the anthropometric data of the user. The frame size calculator 57 typically selects starting seat and handlebar positions from statistical data relating bicycle size to anthropometric data. For this purpose, the bicycle controller 51 is connected to the internet 58, to access a remotely-located server comprising the statistical data tables associating bicycle/frame sizes to anthropometric data. These statistical data tables are typically updated with any new user recording adjusted bicycle dimensions as a function of anthropometric data.

The frame size data calculated by the frame size calculator 57 can represent enough information for a user (e.g., salesman) to select a bicycle of correct size. As an example, the X and Y coordinates of the seat and of the handlebars are given with respect to the pivot axis of the crankset, the reference. A tool (e.g., a t-shaped ruler) may then be provided to measure a bicycle to determine whether it has the right size. Accordingly, a store salesman can readily pick bikes from the inventory by having the required dimensions of the bike, and means to measure the bike.

Alternatively, the user interface 56 may produce data in the form of savable files. For instance, the frame size data may be printed out, or saved, to be sent to a supplier or a manufacturer of bicycles. Similarly, the bicycle controller 51 may be connected to the internet 58, so as to forward bike dimensions to a manufacturer of bicycles. In the case of custom-made bicycles, the delay between the fitting of a bicycle is reduced with the use of the controller system 50.

Additional information can be obtained. For instance, it is considered to place the stationary bicycle 10 in a wind tunnel in order to obtain the rider's drag coefficient as a function of the effect of the size of the bicycle on the riding position. This information is then related to the performance of the rider to determine the optimal size of the bicycle for the rider.

It is also considered to use the stationary bicycle as a motion simulator for video games. The stationary bicycle 10 can provide force feedback in the form of resistance in the exercise wheel 13, as well as through actuation of the actuators 24, 27, 31 and/or 34 to simulate the vibrations of a bicycle.

Figure 6:
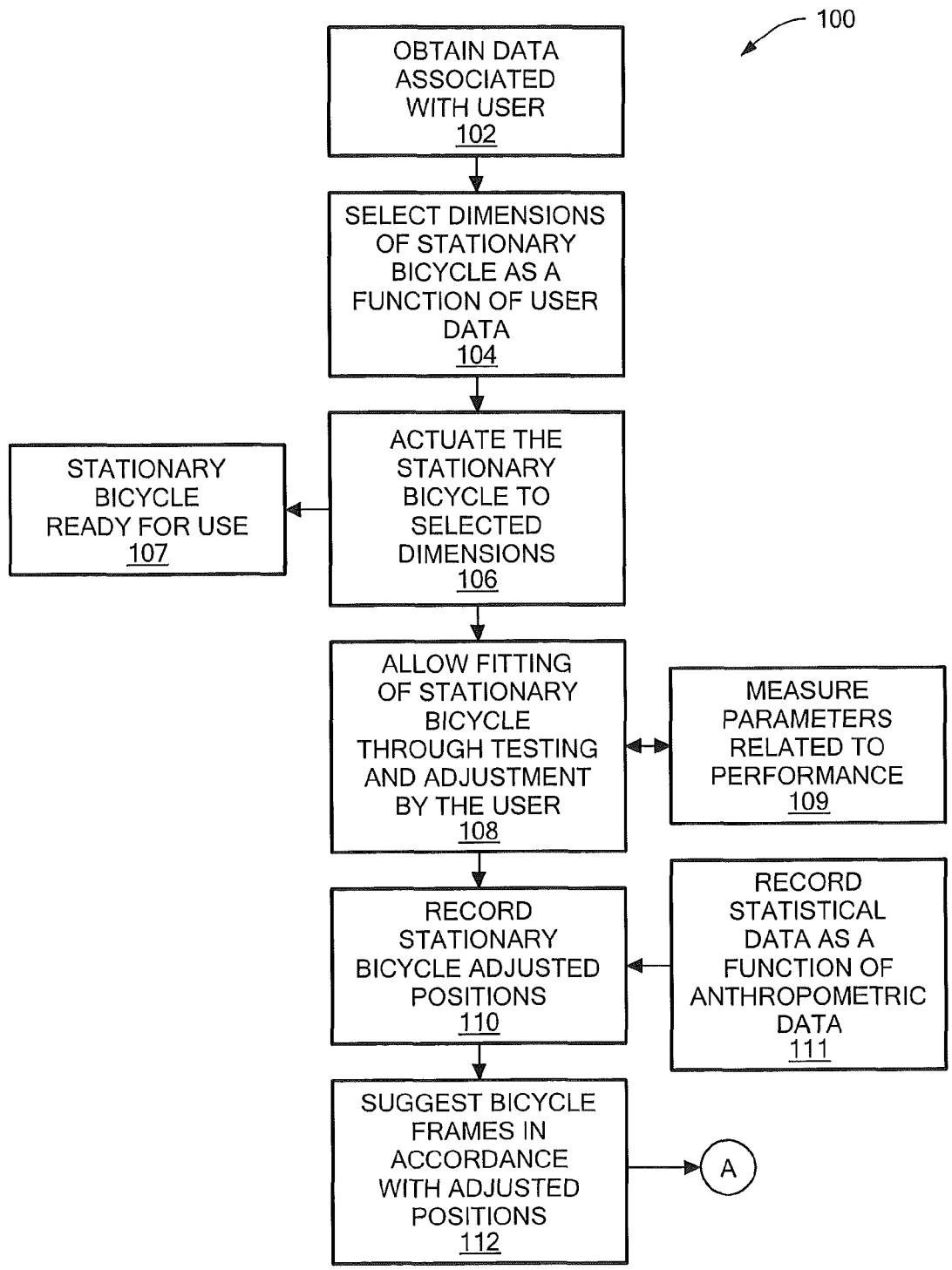
FIG. 6 is a flow chart illustrating a method for adjusting a stationary bicycle in accordance with yet another embodiment of the invention.

In FIG. 6, a method 100 for adjusting a stationary bicycle, such as the stationary bicycle 10 of FIGS. 1 to 4, for instance used in combination with the stationary bicycle control system as described in FIGS. 1 to 5, is explained.

In step 102, data associated with the user of the stationary bicycle is obtained.

In one embodiment, if it is the first time the user tries the stationary bicycle, the data is typically anthropometric data pertaining to the limb length (e.g., measured at the crotch), the torso dimensions, the arm length of the user, the shoulder width. Additional information such as user restrictions (e.g., back pain, knee problems, or the like) may also be recorded.

In another embodiment, in which the stationary bicycle is used in a training environment and the user already has a profile recorded in the stationary bicycle control system 50 (FIG. 5), the data obtained in step 102 is an identification of the user. By obtaining the identification of the user in step 102, the stationary bicycle control system 50 can load stationary bicycle dimensions as prerecorded in a user profile following a previous adjustment session.

In step 104, the dimensions of the stationary bicycle are selected as a function of the user data obtained in step 102. More specifically, if the data is anthropometric in nature, the stationary bicycle control system obtains typical dimensions from statistical data tables relating anthropometric data of numerous users to average dimensions associated with such data. In another embodiment, the selected dimensions of the stationary bicycle are provided with a user profile.

In step 106, the stationary bicycle is actuated to the selected dimensions using the various actuators described in FIGS. 1 to 5.

In step 107, particularly useful when the stationary bicycle is used in a training environment, the stationary bicycle is ready for use. Step 107 is typically achieved if an adjustment fitting of the stationary bicycle was performed in a previous session.

In step 108, a testing period is provided for the stationary bicycle. More specifically, the user spins with the stationary bicycle in order to provide a personal appreciation of the specific selected dimensions. In step 108, the user or an operator (e.g., a trainer) use the interface of the stationary bicycle control system 50 in order to adjust the seat and handlebar position, to reach adjusted positions that are preferred by the user. It is also pointed out that an observer, such as a bike-shop specialist, can stand next to the user to provide comments on the stance and the pedaling style.

In one testing configuration, the adjusted positions are reached after several positions are tested. It is suggested to provide incremental variations of the bicycle dimension, and require that the user spins at a constant power. The comments of the user are gathered at each variation of position, to facilitate the selection of a bicycle size. It is also considered to film the user while pedaling to provide footage of pedaling actuation for different frame dimensions.

In another testing configuration, the adjusted positions are used after gathering parameters related to the performance of the user. More specifically, in optional step 109, measurements are made on parameters related to the performance of the user of the stationary bicycle. For instance, the pedaling power, the pedaling cadence, and the heart rate of the user are measured as a function of the stationary-bicycle dimensions. This step is typically performed for high-level athletes.

In step 110, once testing is completed and the user has elected final dimensions for the stationary bicycle, the adjusted dimensions are recorded for the user. Accordingly, if the stationary bicycle is used in a training environment, a profile specific to the user are recorded, so as to skip testing steps 108 and 109 at the next use.

In optional step 111, statistical data is recorded as a function of the anthropometric data so as to accumulate general data associating bicycle dimensions with anthropometric data.

In step 112, particularly useful for bike-shop use, bicycle-frame dimensions are suggested in accordance with the adjusted positions recorded in step 110.

In one embodiment, the bicycle-frame dimensions may be compared with inventory of a shop so as to determine what bicycles in the shop are suited for the user as a function of the adjusted positions resulting from method 100.

As an alternative embodiment, the bicycle-frame dimensions obtained in step 112 are forwarded to a bicycle manufacturer for the manufacture of a bicycle with such dimensions.

As described above, method 100 is well suited for determining an optimal bicycle size (combination of frame, stem, spacer(s) and seat post) for a given rider. The bicycle-frame dimensions of the determined optimal bicycle size may be compared with inventory of a shop so as to determine a best fit complete bicycle from available bicycles in the shop.

However, when custom fitting a bicycle to a given rider, it is preferable to select each of the frame, stem, spacer(s), and seat post separately, so that an optimal combination of components can be determined. As used herein, selection or determination of a spacer(s) includes the selection or determination of no spacer, or one or more spacers.

To better accommodate custom fitting, the bicycle controller system 50 includes a database 200 (see FIG. 5) for storing dimensions of bicycle frames, stems, spacers, and seat posts that are available for use, whether such availability is from shop inventory of the shop doing the custom fitting, or from other avenues of procurement, such as a manufacturer's inventory, or inventory of another shop that participates in a parts-exchange program. As discussed above, the information contained within database 200 may alternatively be accessed from an external database via internet server 58.

Figure 7:
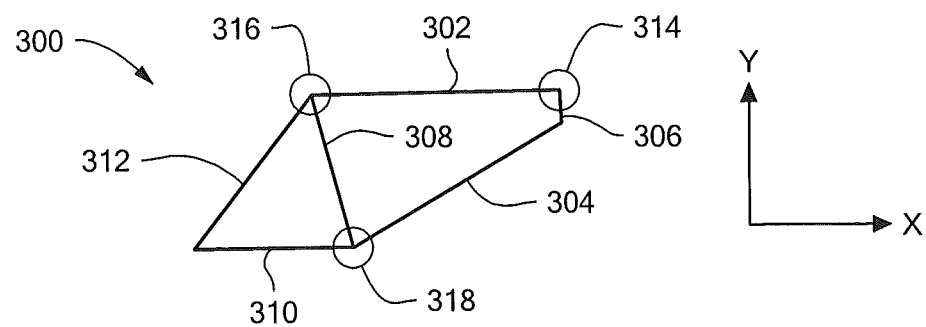
FIG. 7 depicts a one-line diagram representation of a bicycle frame having features related to features of the adjustable stationary bicycle of FIG. 1.
Figure 8:
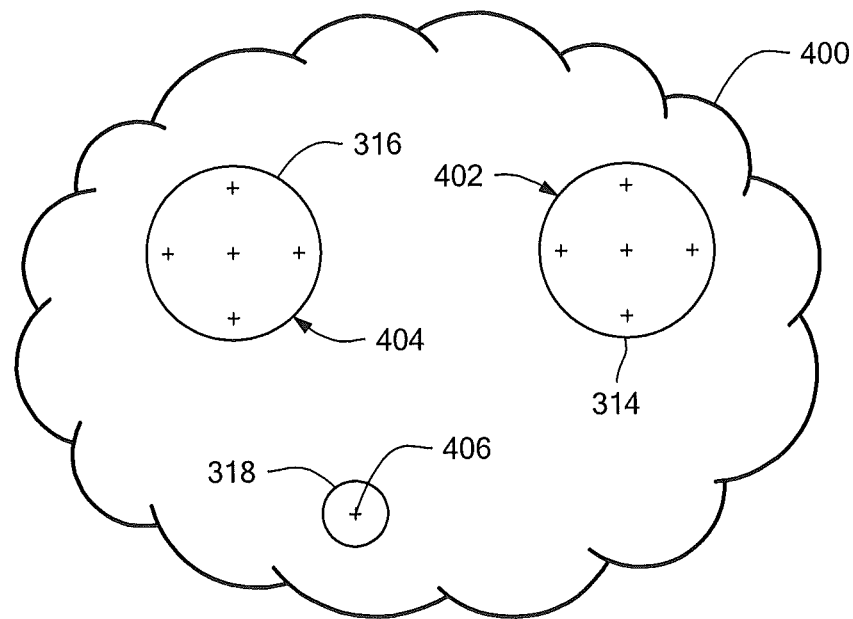
FIG. 8 depicts a first cloud of points that represent the X,Y coordinates of the top of a head tube, and the X,Y coordinates of the top of a seat post, relative to a central axis of a bottom bracket, for all bicycle frames that are available to a fitter, for use in accordance with an embodiment of the invention.

The dimensions of the available bicycle frames are stored in database 200 in a "cloud of points" format, best seen with reference to FIGS. 7 and 8, where FIG. 7 depicts a one-line diagram representation of a bicycle frame 300 having a top tube 302, a down tube 304, a head tube 306, a seat tube 308, chain stay tubes 310, and seat stay tubes 312, all disposed and attached to each other in a manner known in the art, and FIG. 8 depicts an aggregate cloud of points 400 (also herein referred to as a first cloud of points) that represent the X, Y coordinates of the top of the head tube 402, and the X, Y coordinates of the top of the seat post 404, relative to the central axis of the bottom bracket 406, for all frames 300 that are available to the custom fitter. The graphic circles 314, 316 and 318 relate the features of frame 300 depicted in FIG. 7 with the associated cloud of points 402 and 404 depicted in FIG. 8. As can be seen from the illustration of FIG. 8, there is only one X, Y coordinate for the bottom bracket of each available frame, as this X, Y coordinate in used as the reference discussed above in connection with the center of the crankset 14.

The dimensions of the available stems and spacers, and the dimensions of the available seat posts, are also stored in database 200 in respective cloud of points formats, which will be discussed in more detail below.

Figure 9:
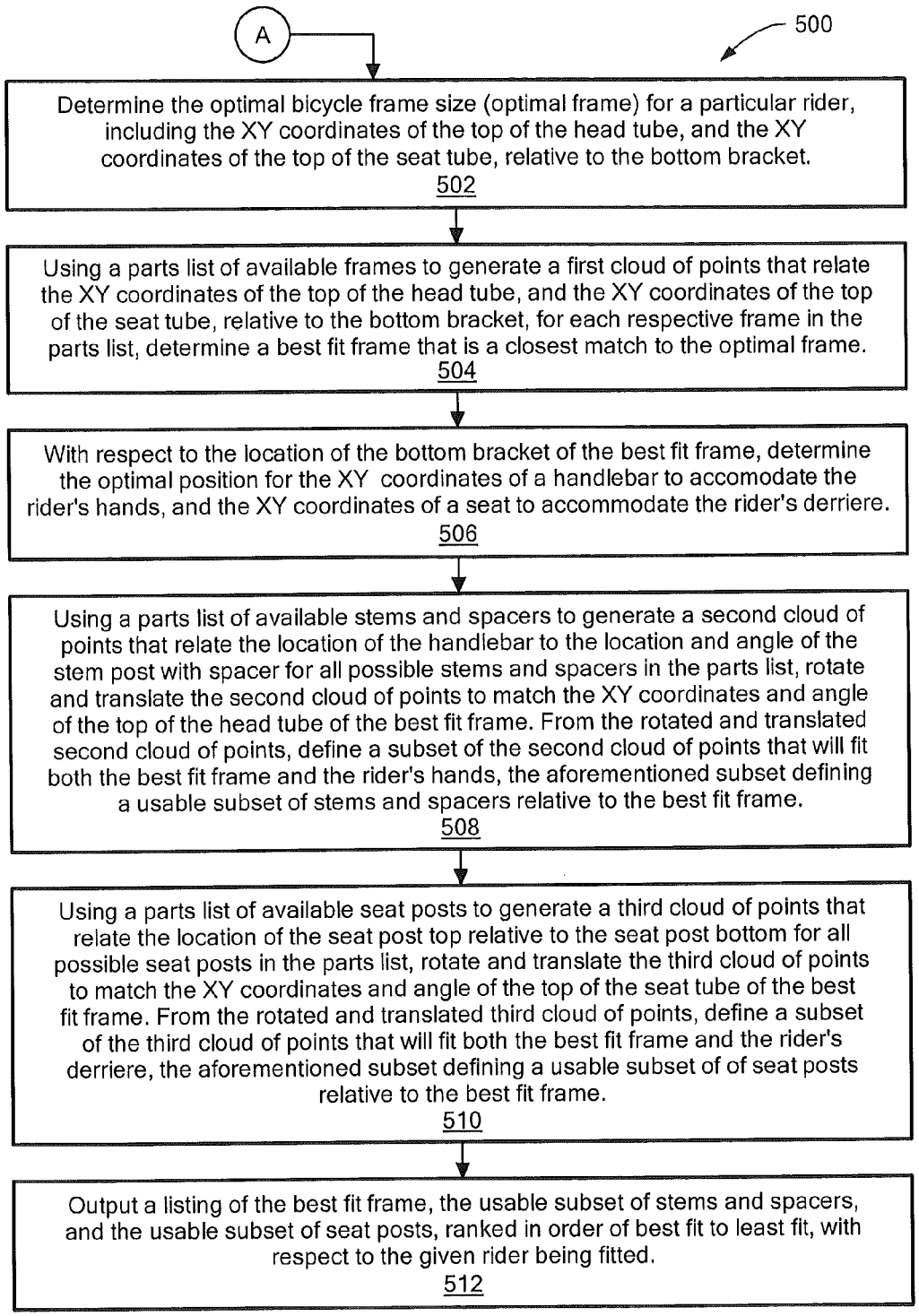
FIG. 9 depicts a flow chart illustrating a method for determining a best fit bicycle from a multitude of available bicycle frames, stems, spacers and seat posts, in accordance with an embodiment of the invention.

Referring now to FIGS. 6 and 9, an extension of method 100 is seen represented in FIG. 6 by a circle-A graphic after step 112, which is repeated in the extended method 500 depicted in FIG. 9 before step 502. In an embodiment that will now be described in more detail, method 500 is an extension of method 100.

At step 502, method 500 begins where method 100 ends, while utilizing information gathered and/or suggested by method 100. For example, in step 112 of method 100, bicycle-frame dimensions are suggested in accordance with the adjusted positions recorded in step 110. As discussed above, the suggested bicycle-frame dimensions include an optimal frame size that is determined by the frame size calculator 57, which includes optimal X, Y dimensions for the location of the top of the head tube 306 and the top of the seat tube 308 relative to the reference, center of the crankset 14, also herein referred to by reference numerals 318 and 406. However, it is quite possible that the optimal X, Y dimensions for the suggested bicycle-frame include dimensions that are not exactly available in an off-the-shelf or stock bicycle frame. As such, a further methodology is required to establish a best-fit bicycle frame and associated bicycle components (stem, spacer, seat post) that are appropriate for a given rider being fitted. Such further methodology is found in method 500 and performed by the above mentioned expanded functionality of frame size calculator 57.

At step 502, the optimal bicycle frame size (optimal frame) for a particular rider is determined from the information available at step 112. The optimal frame size includes the XY coordinates of the top of the head tube 306, and the XY coordinates of the top of the seat tube 308, relative to the bottom bracket 406. As discussed previously, the optimal frame that is determined at step 502 may not actually be available in an off-the-shelf or stock bicycle frame, which leads to step 504.

At step 504, a best fit frame that is a closest match to the optimal frame is determined. In order to accomplish this best fit determination, the parts list of available frames stored in database 200, which includes the head tube angle (HT Angle) and XY coordinates of the top of the head tube 306, and the seat tube angle (ST Angle) and the XY coordinates of the top of the seat tube 308, relative to the bottom bracket 406, is used to generate the first cloud of points 400 that relate the XY coordinates of the top of the head tube (see FIG. 8 cloud of points 402), and the XY coordinates of the top of the seat tube (see FIG. 8 cloud of points 404), relative to the bottom bracket (see FIG. 8 reference 406), for each respective frame in the parts list. The HT Angle and the ST Angle are used in a manner that will be described in more detail below. The end result of step 504 is the identification of an available off-the-shelf best fit bicycle frame that is a closest match to the aforementioned optimal frame from step 502.

At step 506, a determination is made of the optimal position for the XY coordinates of a handlebar to accommodate the rider's hands, and the XY coordinates of a seat to accommodate the rider's derriere, relative to the location of the bottom bracket 406 of the best fit frame. This determination may be made with the assistance of the frame size calculator 57 that is discussed above as identifying initial seat and handlebar positions from the anthropometric data of the user being fitted, or with information from sensors 202, 204, 206, 208 (see FIG. 5) that provide the XY coordinates of the handlebar and seat as discussed above.

Figure 10:
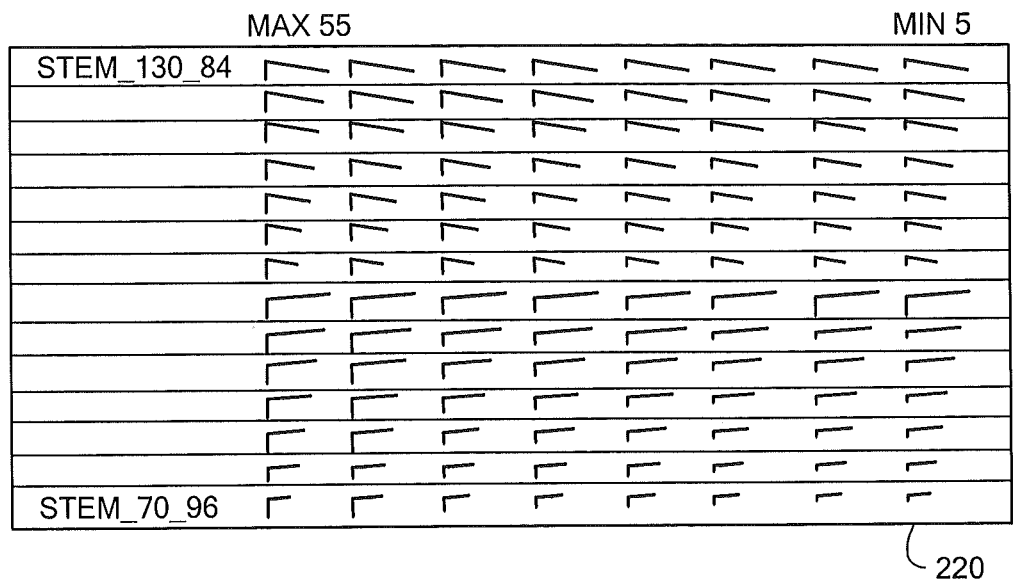
FIG. 10 depicts a matrix representation of all available bicycle stems, in accordance with an embodiment of the invention.
Figure 11:
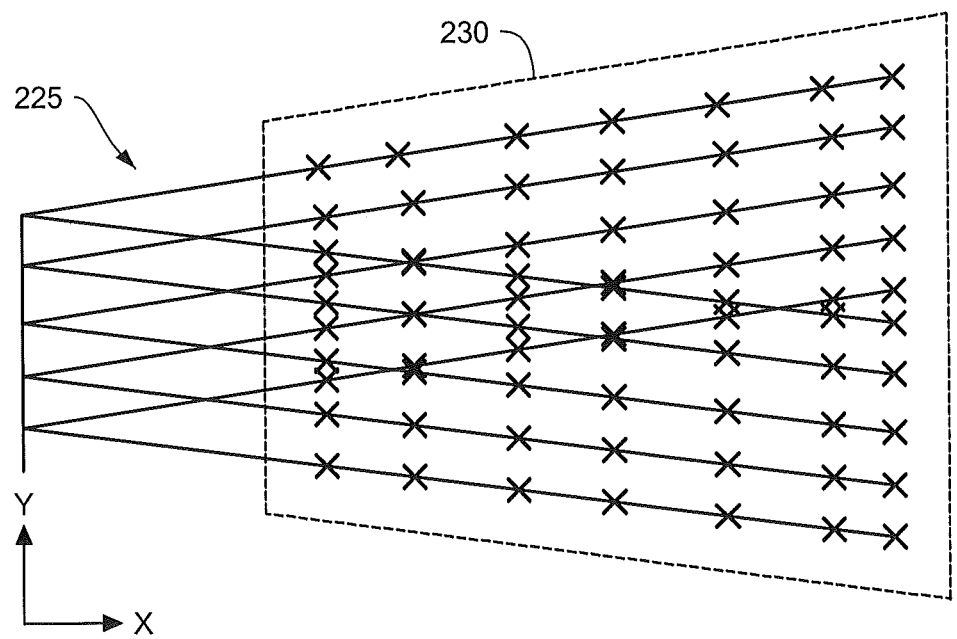
FIG. 11 depicts a one-line diagram representation of the available stems of FIG. 10 in combination with all available spacers overlaid on top of each other, where the X's depict a second cloud of points representative of the location where a handlebar would attach to the end of a respective stem, in accordance with an embodiment of the invention.
Figure 12:
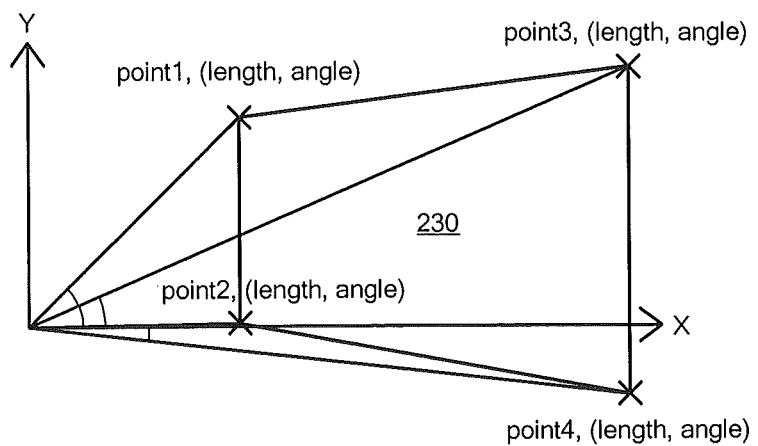
FIG. 12 depicts the outer boundaries of the second cloud of points from FIG. 11.
Figure 13:
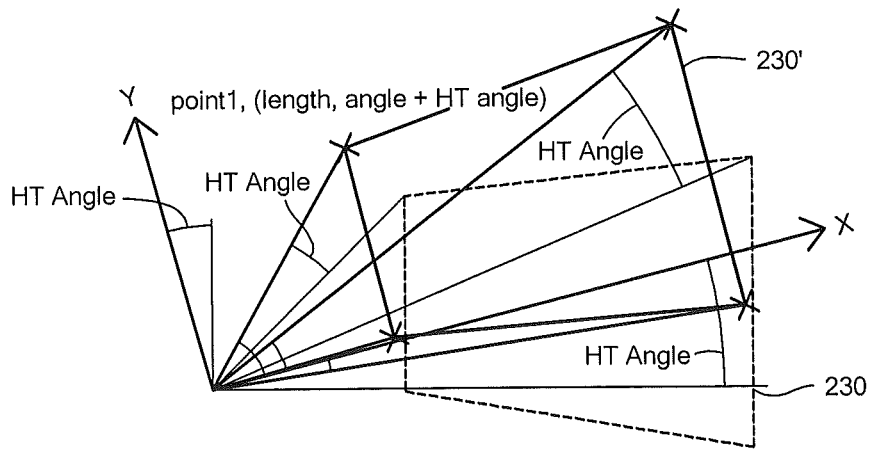
FIG. 13 depicts the second cloud of points from FIG. 12 rotated to the angle of the head tube (HT Angle) of the best fit frame from FIG. 9, in accordance with an embodiment of the invention.

The dimensions of all available stems and spacers are stored in database 200 in a cloud of points format, best seen with reference now to FIGS. 10-13. FIG. 10 depicts a matrix representation 220 of all available bicycle stems. FIG. 11 depicts a one-line diagram representation 225 of the available stems in combination with all available spacers overlaid on top of each other so that the vertical portion of each stem is oriented relative to a vertical Y-axis, where the end of the stem portion that fits in the heat tube provides a common reference, and where the X's depict a cloud of points 230 (also herein referred to as a second cloud of points) representative of the location where the handlebar would attach to the end of a respective stem. FIG. 12 depicts the outer boundaries of the cloud of points 230. And FIG. 13 depicts the cloud of points 230 of FIG. 12 rotated to the angle of the head tube (HT Angle) of the best fit frame, the rotated cloud of points being referred to by reference numeral 230'. From the foregoing it will be appreciated that a parts list of available stems and spacers is used to generate the second cloud of points 230 that relate the location of the handlebar to the location and angle of the stem with spacer for all possible stems and spacers in the parts list, and that a transformation process is applied to generate the rotated and translated second cloud of points 230' so that it is oriented with respect to the XY coordinates and angle of the top of the head tube of the best fit frame.

Similarly, the dimensions of all available seat posts are stored in database 200 in another cloud of points format, best seen with reference now to FIGS. 14A, 14B, 15A, 15B. FIG. 14A depicts a one-line diagram representation 240 of the available (straight) seat posts overlaid on top of each other and oriented relative to a vertical Y-axis, where the bottom of each seat post provides a common reference, and where the X's depict a cloud of points 245 (also herein referred to as a third cloud of points) representative of the location of where the seat would attach to the end of a respective seat post. FIG. 14B depicts a graphical representation 250 of another type of seat post having a rearward clamp head 252. And FIG. 15A depicts the cloud of points 245 of FIG. 14A rotated to the angle of the seat tube (ST Angle) of the best fit frame, the rotated cloud of points being referred to by reference numeral 245'. From the foregoing it will be appreciated that a parts list of available seat posts is used to generate the third cloud of points 245 that relate the location of the seat post top to the seat post bottom for all possible seat posts in the parts list, and that a transformation process is applied to generate the rotated and translated third cloud of points 245' so that it is oriented with respect to the XY coordinates and angle of the top of the seat tube of the best fit frame. FIG. 15B depicts another cloud of points 255' rotated in a manner similar to the cloud of points 245' depicted in FIG. 15A, but where the X's represent the location of where the offset seat would attach to the end of the respective seat post having the aforementioned rearward clamp head 252. It will be appreciated that the aforementioned parts list of available seat posts used to generate the rotated third cloud of points may include only the straight seat posts (rotated cloud of points 245'), only the seat posts having a rearward clamp head (rotated cloud of points 255'), or both (rotated cloud of points 245' and 255').

With reference now back to FIG. 9 at step 508, and from the rotated and translated second cloud of points 230' discussed above, a subset of the second cloud of points 230' that will fit both the best fit frame and the rider's hands is determined by overlaying the XY coordinates of the rider's hands obtained from sensors 206, 208 with the rotated and translated second cloud of points 230' to find a best fit scenario, this subset defining a usable subset of stems and spacers relative to the best fit frame.

At step 510, and from the rotated and translated third cloud of points 245' discussed above, a subset of the third cloud of points 245' that will fit both the best fit frame and the rider's derriere is determined by overlaying the XY coordinates of the rider's seat position obtained from sensors 202, 204 with the rotated and translated third cloud of points 245' to find a best fit scenario, this subset defining a usable subset of seat posts relative to the best fit frame.

At step 512, a listing of the best fit frame, the usable subset of stems and spacers, and the usable subset of seat posts, ranked in order of best fit to least fit, with respect to the given rider being fitted, is output via user interface 56 (see FIG. 5). The first set of bicycle frames presented is called "closest fit", next set is "matching fit", and last is "not fit". Within each of those presentations the fitter can sort by the associated model/frame size, brand, seat distance, handlebar distance, and total distance, with the last three distances being the delta between the DFU XY and the achievable XY on a bicycle, best seen with reference to FIG. 24 discussed below.

It is noteworthy that step 506 includes a determination of both the location of the handlebar (rider's hands) and the location of the seat (rider's derriere) relative to the best fit frame, meaning that method 500 can easily be adapted to pivot the data around either of the components (stem or seat post) to arrive at the output list of step 512.

Furthermore, and while steps 508 and 510 are presented in a particular sequence, it will be appreciated that this particular sequence is not a necessary feature of method 500, and that the order of steps 508, 510 could be reversed.

Implementation of method 500, which augments method 100, is accomplished via user interface 56 (see FIG. 5) having graphical user interface input/selection fields and output display fields, which will now be discussed with reference to FIGS. 16-24.

Figure 16:
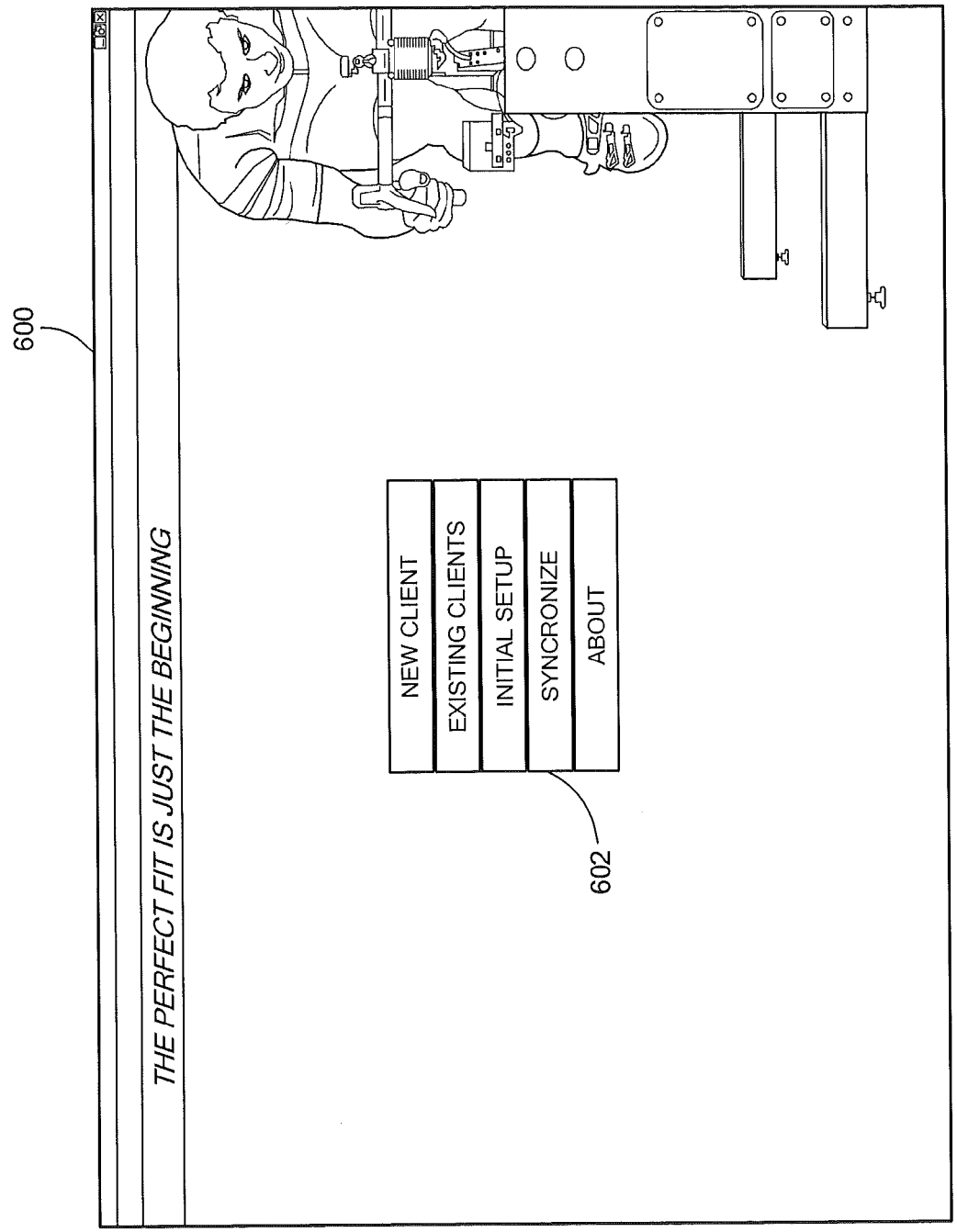
FIG. 16 depicts a first screen image, in accordance with an embodiment of the invention.

FIG. 16 depicts a screen image 600 displayed on user interface 56 and having user selection fields 602 that include "New Client", "Existing Clients", "Initial Set-Up", "Synchronize", and "About". Selecting "New Client" opens the screen image 650 of FIG. 17, which enables a user to input anthropometric data relating to the person being fitted. Selecting "Existing Client" enables a user to select a set of pre-entered anthropometric data relating to the person being fitted. Selecting "Initial Set-Up" opens screen image 800 of FIG. 20 (discussed below), which enables a user to start entering data relating to the best fit bike being determined. Selecting "Synchronize" connects the client side of method 500 (driven by image screens 600, 650, 700, 750, 800, 850, 900, 950, 1000 of FIGS. 16-24 discussed in more detail below), which is locally hosted on a bicycle fitter's computer that runs the DFU (such as bicycle controller system 50 for example), to database 200 or the database housed on the server 58, uploading all fitting data from the local machine 50 to the server 58. This data can then be accessed either at the server level, or replicated on another local computer using unique identifier associated with that shop's data. Selecting "About" opens a screen image (not shown) that presents information about the software that is running, such as version number for example.

Figure 17:
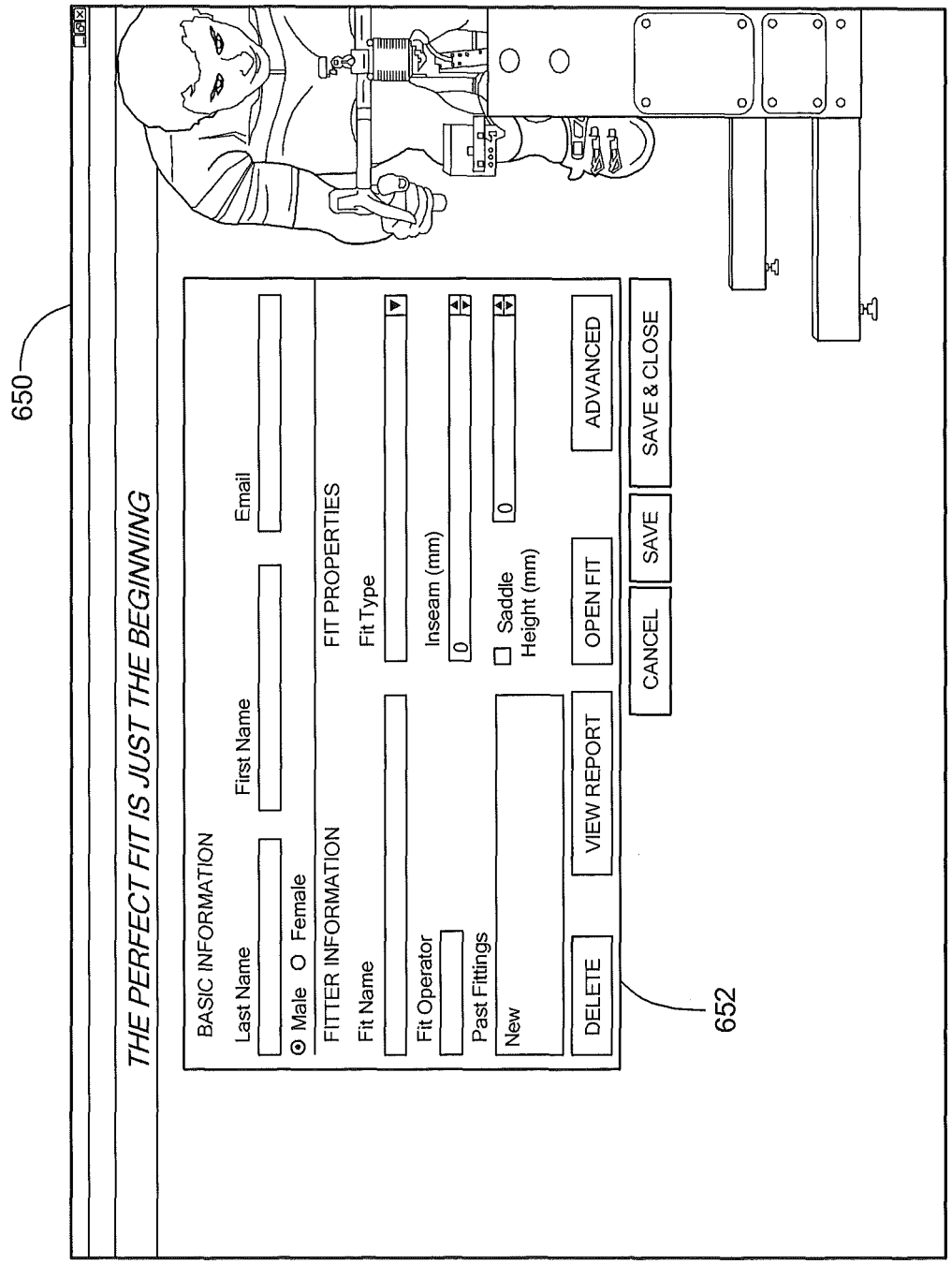
FIG. 17 depicts a second screen image, in accordance with an embodiment of the invention.

FIG. 17 depicts a screen image 650 having input/selection fields 652 relating to "Basic Information", "Fitter Information", and "Fit Properties", and selection buttons directed to "Delete", "View Report", "Open Fit", "Advanced", "Cancel", "Save", and "Save & Close". "Male"/"Female" radio buttons provide for the appropriate selection of one. The "Basic Information" section includes input fields directed to the "Last Name", "First Name" and "Email" address of the person being fitted. The "Fitter Information" section includes input fields directed to the "Fit Name" used to identify the particular data being entered, the "Fit Operator" who is performing the fit procedure, and any listing of "Past Fittings" that may exist for the particular person being fitted. The "Fit Properties" section includes input fields directed to the type of bike being fitted, herein referred to as "Fit Type", the "Inseam" of the person being fitted entered in millimeters, and the "Saddle Height" of the person being fitted, if known, entered in millimeters (selection of a check box enables entry of the saddle height in millimeters). Selection of a "Fit Type"

is made via a drop down menu that permits selection of such types as road, triathlon, time trial, mountain, cross country, trail, and cyclocross, to name a few. The "Inseam" and "Saddle Height" selections are made via up/down selection arrows. Selection of the "Delete" button deletes all data entered on the screen 650. Selection of the "View Report" button provides a summary report of all data input on the screen. Selection of the "Open Fit" button opens screen 850 of FIG. 21 (discussed below), which starts and controls the fitting process. Selection of the "Advanced" button opens screen 700 of FIG. 18 (discussed below). Selection of the "Cancel" button cancels further operation of the fitting program. Selection of the "Save" button saves any data entered at that point in time. Selection of the "Save & Close" button saves any data entered at that point in time and closes the fitting program.

Figure 18:
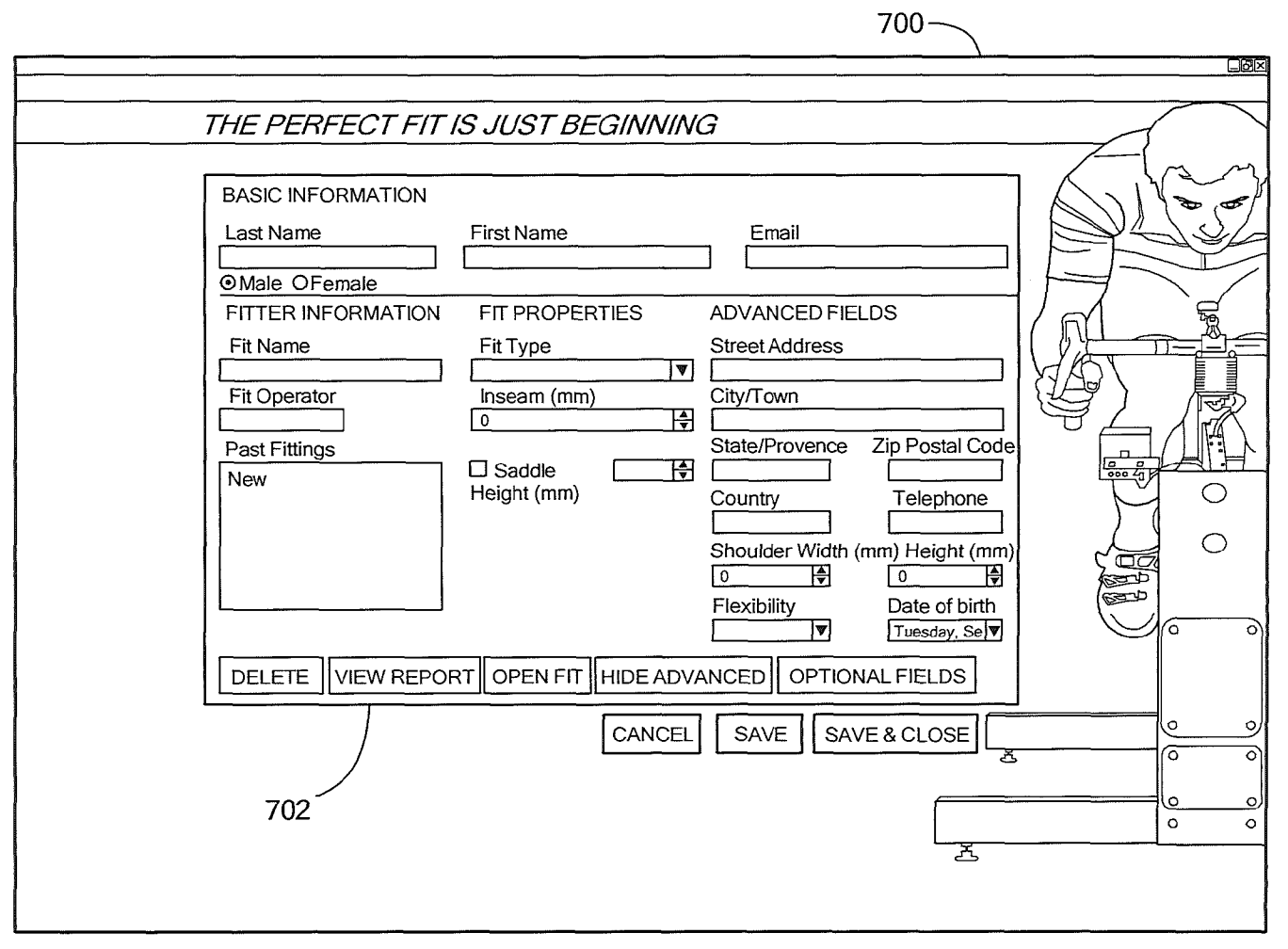

FIG. 18 depicts a screen image 700 having input/selection fields 702 that are similar to and in addition to the input/selection fields 652 of FIG. 17. Only the additional input/selection fields are further described herein as like input/selection fields have like functionality. An additional section presented in screen image 700 is directed to "Advanced Fields", which includes input fields directed to the "Street Address", "City/Town", "State/Province", "Zip/Postal Code", "Country", "Telephone", "Shoulder Width (mm)", "Height (mm)", "Flexibility", and "Date of Birth" relating to the person being fitted. Additional selection buttons presented in screen image 700 include "Hide Advanced", which when selected hides the "Advanced Fields" section, and "Optional Fields", which when selected opens screen 750 of FIG. 19 (discussed below).

Figure 19:
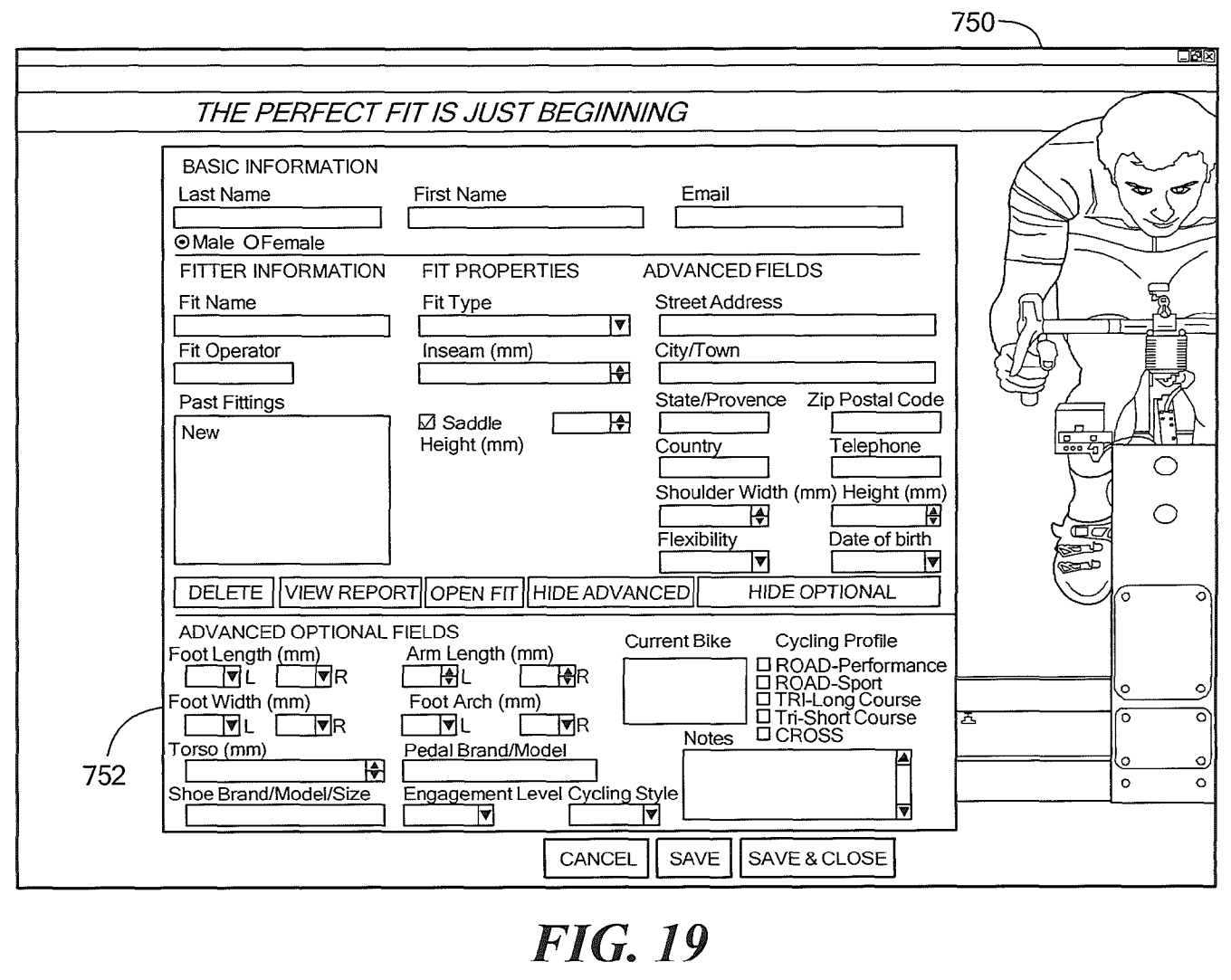

FIG. 19 depicts a screen image 750 having input/selection fields 752 that are similar to and in addition to the input/selection fields 702 of FIG. 18. Only the additional input/selection fields are further described herein as like input/selection fields have like functionality. An additional section presented in screen image 750 is directed to "Additional Optional Fields", which includes input fields directed to the "Foot Length (mm)" left (L) and right (R), "Foot Width (mm)" left (L) and right (R), "Foot Arch (mm)" left (L) and right (R), "Arm Length (mm)" left (L) and right (R), "Torso (mm)", "Pedal Brand/Model", "Shoe Brand/Model/Size", "Engagement Level", "Cycling Style", "Current Bike", "Cycling Profile", and "Notes" relating to the person being fitted. As illustrated, graphical user interface drop down menus and up/down selection arrows may be employed in a manner know in the art. A "Hide Optional" selection button when selected hides the "Optional Fields" section.

Figure 20:
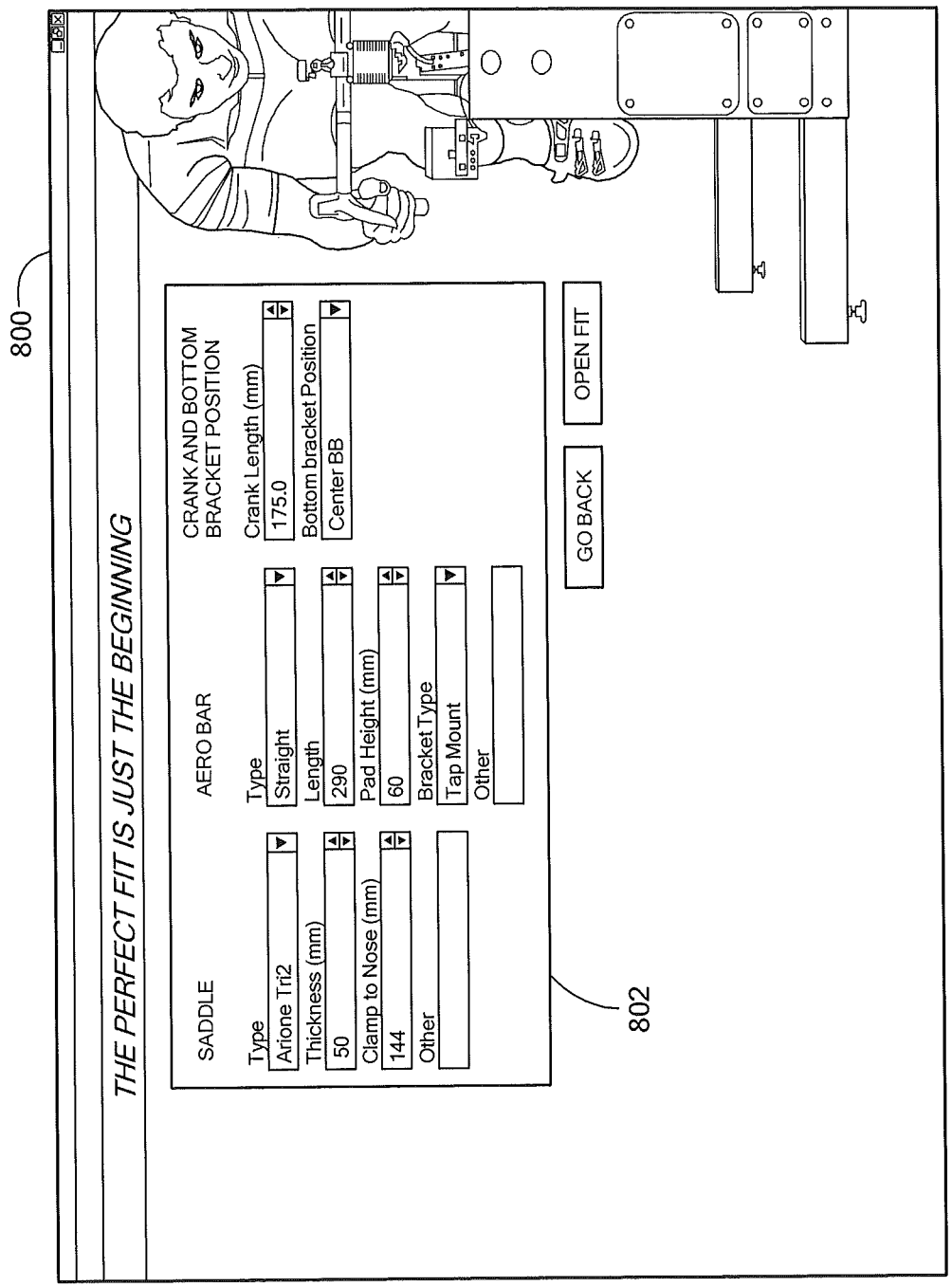
FIG. 20 depicts a fifth screen image, in accordance with an embodiment of the invention.

FIG. 20 depicts a screen image 800 that is also referred to as the Start Setup screen, and includes input/selection fields 802 directed to information relating to "Saddle", the "Aero Bar", and the "Crank And Bottom Bracket Position", if such information is known. Drop down menus and up/down selection arrows are employed as appropriate for a purpose disclosed herein. Information relating to the "Saddle" includes the "Type" of saddle, the "Thickness (mm)" of the saddle, the "Clamp to Nose (mm)" dimension of the saddle, and any "Other" information about the saddle that may be pertinent for purposes of fitting. Information relating to the "Aero Bar" includes the "Type" of aero bar, such as straight for example, the "Length" of the aero bar, the "Pad Height (mm)" of the aero bar, the "Bracket Type" for mounting the aero bar, such as top mount for example, and any "Other" information about the aero bar that may be pertinent for purposes of fitting. Information relating to the "Crank And Bottom Bracket Position" includes the "Crank Length (mm)" in millimeters, and the "Bottom Bracket Position", such as center bottom bracket for example. "Go Back" and "Open Fit" selection buttons are provided to either open the previous screen, or advance to the Fitting Control screen of FIG. 21 (discussed below).

Figure 21:
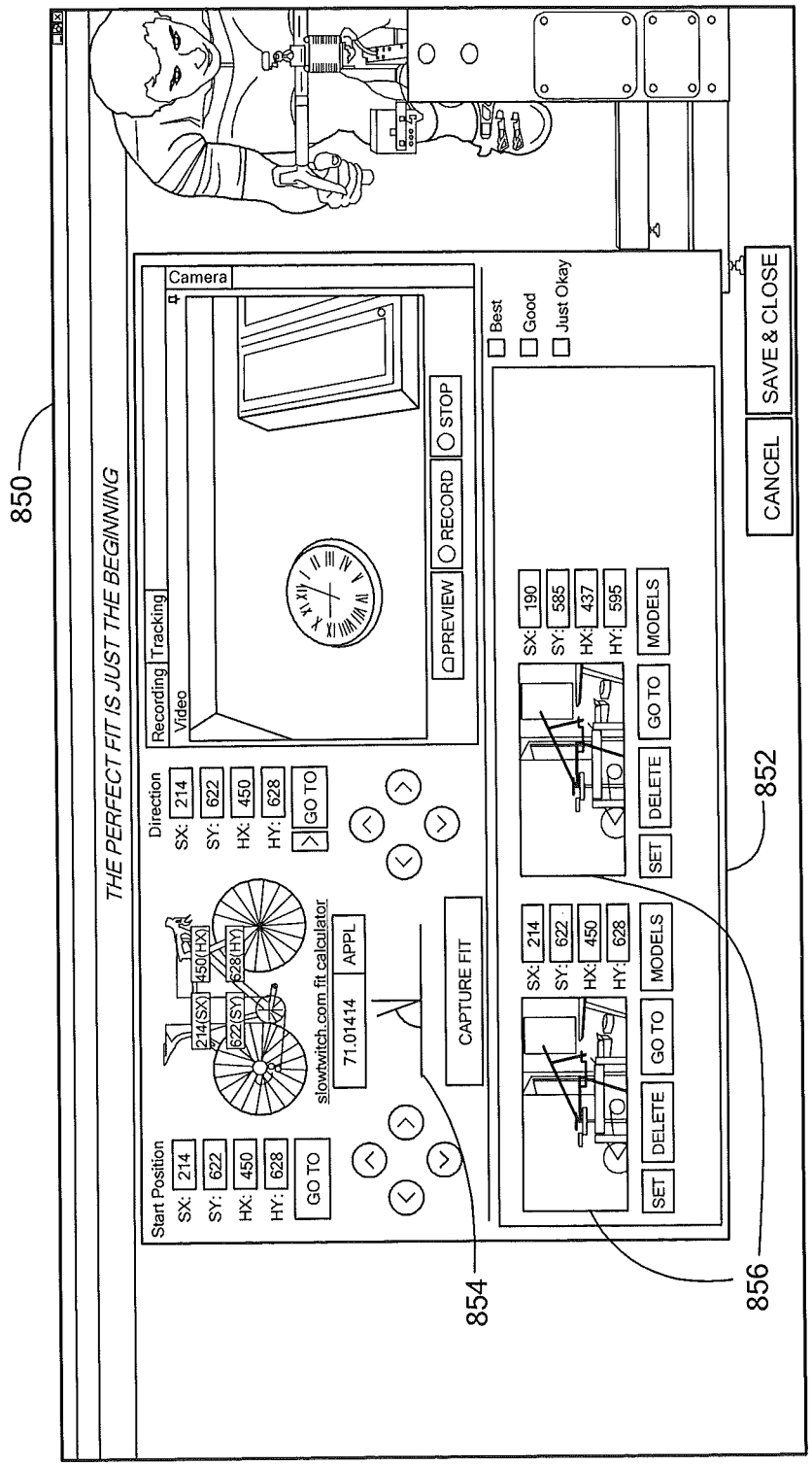
FIG. 21 depicts a sixth screen image, in accordance with an embodiment of the invention.

FIG. 21 depicts a screen image 850 that is also referred to as the Fitting Control screen. Inputs and/or changes made to the Fitting Control screen 850 are received by the bicycle controller 51 of the bicycle controller system 50 (see FIG. 5), which in turn provides control signals to the position commander 52, which in turn provides control signals to actuate the actuators 24, 27, 31, 34, which in turn move the seat and handlebars along XY axes according to the fitting parameters entered on the Fitting Control screen 850. The left side of the Fitting Control screen 850 provides graphical control for adjusting the DFU 10, herein referred to as the Control Section, while the right side of the Fitting Control screen 850 provides video recording and tracking of the athlete on the DFU, herein referred to as the Video Section. This video can be analyzed to measure key joint angles of the athlete, such as leg extension and hip angle, and can be done either in a static or dynamic fashion. Further, every time the fitter selects the "Capture Fit" button (discussed further below), the software collects the SX, SY, HX, and HY coordinates, along with a still image of that athlete represented by stick FIG. 856 in that position. Multiple positions can be stored and reviewed at a later time, with the associated image always being shown in the captured fit window. The Control Section includes input parameters for the "Start Position" of, and the "Direction" of change of, the seat and the handlebars, where the X, Y position of the seat relative to the bottom bracket is denoted by SX, SY, and the X, Y position of the handlebars relative to the bottom bracket is denoted by HX, HY. The X and Y positions of the seat are adjusted by clicking on the up/down/left/right buttons on the left side of the Control Section, and the X and Y positions of the handlebars are adjusted by clicking on the up/down/left/right buttons on the right side of the Control Section. The SX, SY, HX, and HY coordinates can also be altered by changing the numerical values in the boxes located below the "Direction" or "Start Position" buttons and using the "Go To" buttons, which will then move the DFU to the specified position via actuators. In so doing, all four axes, or any combination of them, can be moved simultaneously. 24, 27, 31, 34. A graphical indication of how well the best fit frame determination compares to the optimal frame determination is provided by graphic 854, which in an embodiment is also color coordinated such that a "green" color indicates a "best fit" scenario, a "blue" color indicates a "good" fit scenario, and an "orange" color indicates a "just okay" fit scenario. In an embodiment, the color indication of graphic 854 may be replaced with a non-color indication, such as the graphic 854 having a "solid" line being synonymous with the graphic 854 being "green" in color, the graphic 854 having a "dashed" line being synonymous with the graphic 854 being "blue" in color, and the graphic 854 having a "dotted" line being synonymous with the graphic 854 being "orange" in color. In another embodiment, the graphic 854 may include both color and line weight as a visual indicator of the fit scenario. Once the fit is determined to be acceptable, the "Capture Fit" button is selected, which stores the fit information in database 200 and initiates method 500 to determine the best-fit bicycle for the person being fitted. If multiple positions have been stored using the "Capture Fit" button the fitter has the ability to use the "Go To" button on the captured fits to toggle between the various positions, with the DFU moving all axes simultaneously to move to the saved position. This allows the person being fitted to feel the difference from one position to another in real time with no need to stop pedaling or dismount the DFU. An "APPLY" selection button is provided in the Control Section to allow for the fitter to execute a fit using a Fit Institute Slowtwitch (F.I.S.T.) fitting protocol in a seamless fashion. This protocol uses a technique which optimizes the position of the rider at a given seat tube angle, and then tests the rider across multiple effective seat tube angles, while maintaining the relationship of the saddle and handlebars at those different seat tube angles. The information in the box next to and on the left side of the "Apply" button is the effective seat tube angle of the position the rider that is currently on the DFU. This angle can be changed by the fitter by typing in the desired angle, and the software will do all necessary calculations to adjust the entire position, moving all 4 axes simultaneously to maintain the relationship between the saddle and handlebars and the resultant biomechanical alignment of the athlete/rider. In so doing, the fitter is able to test the rider's position across a range of seat tube angles quickly without the fitter having to do the calculations for the effective geometric relationships between the 4 axes (relating to SX, SY, HX, HY). All other fit cycles require the fitter to do these calculations independent from the fit cycle and then apply the results manually. As the F.I.S.T. protocol relies on a "good, better, best" approach to determining at which seat tube angle a rider is most comfortable, the ability to seamlessly move the rider back and forth between saved positions allows for the execution of this fitting more efficiently than a manually adjusted fit cycle.

Figure 22:
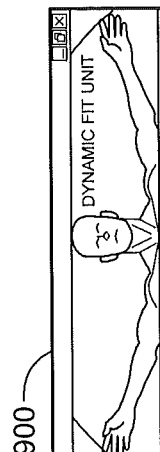
FIG. 22 depicts a seventh screen image, in accordance with an embodiment of the invention.

FIG. 22 depicts a screen image 900 that provides best fit output information from method 500. "Available Models" that fit a best-fit scenario (ranked according to the above noted "best fit", "good" fit, and "just okay" fit categories) are presented on the top of screen image 900, and "Selected Models" from the Available Models are presented in more detail, providing part names for the best-fit frame, stem, and seat post, for example, on the bottom of screen image 900.

Figure 23:
FIG. 23 depicts a eighth screen image, in accordance with an embodiment of the invention.

FIG. 23 depicts a screen image 950 that provides more details relating to the Selected Model from screen image 900.

Figure 24:
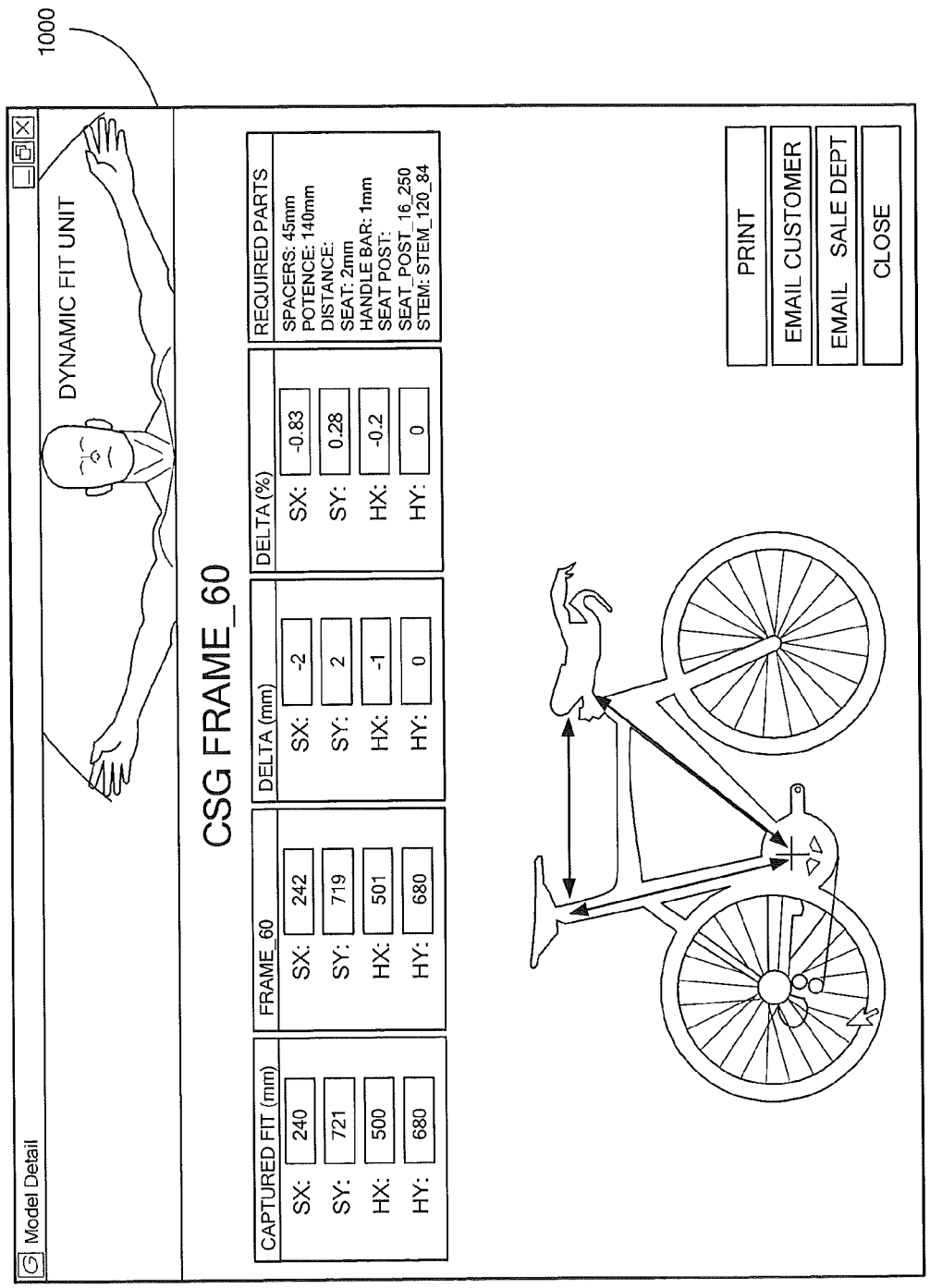
FIG. 24 depicts a ninth screen image, in accordance with an embodiment of the invention.

FIG. 24 depicts a screen image 1000 that provides a customer report of the best-fit bicycle parameters as compared to the optimal bicycle parameters. In the embodiment illustrated, "Capture Fit (mm)" correlates with the optimal bicycle from method 500, and "Frame_60" correlates with the best-fit bicycle determined from method 500. It will be appreciated that the "Frame_60" naming convention is only for illustration purposes. The information presented in "Delta (mm)", and optionally "Delta (%)", provides numerical values for the amount of difference between the optimal and best-fit bicycles. The required parts for the stem, spacer(s) and seat post, needed to build the best-fit bicycle are provided under "Required Parts" listing. Screen image 1000 also includes selection buttons to print the customer report via the "Print" selection button, email the customer report via the "Email Customer" selection button, email the sale department via the "Email Sale Dept." selection button, and close the DFU program via the "Close" selection button.

In addition to the foregoing description of method 500 that determines a best-fit bicycle frame, stem, spacer(s), and seat post for a rider being fitted, another feature that frame size calculator 57 is capable of performing is the determination of available riding apparel suitable for the rider being fitted. Since anthropometric data of the rider is captured in one or more of image screens 600, 650, 700, 750, 800, 850, 900, 950, 1000, and saved in database 200, a comparison of available riding apparel in inventory, also saved in database 200, to the anthropometric data of the rider will easily accomplish the task of finding appropriate apparel that will fit the rider. In this way, not only can the rider be fitted with an appropriately sized bicycle, but can also be fitted with appropriately sized apparel, such as riding shoes, socks, shorts, top, jacket, sun glasses, and helmet, for example.

An algorithm available at http://paulbourke.net/geometry/insidepoly/ that finds a point inside a polygon in a two-dimensional plane, and commercially available algorithms utilized by GPS mapping software to locate an address, or latitude/longitude coordinate, are examples of mathematical theories upon which the software implementing method 500 is based, with the exception that method 500 applies a cloud of points format to the data under analysis to determine a best fit scenario for not only the frame, but also for the stem, spacer(s) and seat post. A complete bicycle is typically built from a frame, a stem, a seat post and spacers (between 0 spacer and 10 spacers, which in an embodiment are 5 mm for each spacer). The part that has the most variation is the frame because the seat angle, handlebar angle, handlebar size (X,Y location of handlebar relative to bottom bracket), and seat post (X,Y location of seat relative to bottom bracket) are variable. Applying all stems and seat posts to all frames can lead to performance issues. In order to simplify the selection process, all stem possibilities (including all spacers' possibilities) and all seat post possibilities are replaced by a polygon that contains all single X,Y coordinates (one polygon for all seat posts and one polygon for all stem and spacers). The two polygons are then applied to each frame by applying the handlebar angle, handlebar X,Y coordinate, seat angle, and seat post X,Y coordinate. FIG. 12 represents the polygon of all stems and spacers in two dimensions. FIG. 13 represents the polygon applied to one frame based on the handlebar angle. A reference made herein to the X,Y location of a seat post means a reference to the X,Y location of the center of the seat post clamp (see FIG. 14B, item 252, for example) for clamping the seat to the seat post, and a reference to the X,Y location of the top of the seat post means a reference to the X,Y location of the center of the seat post clamp.

Figure 25:
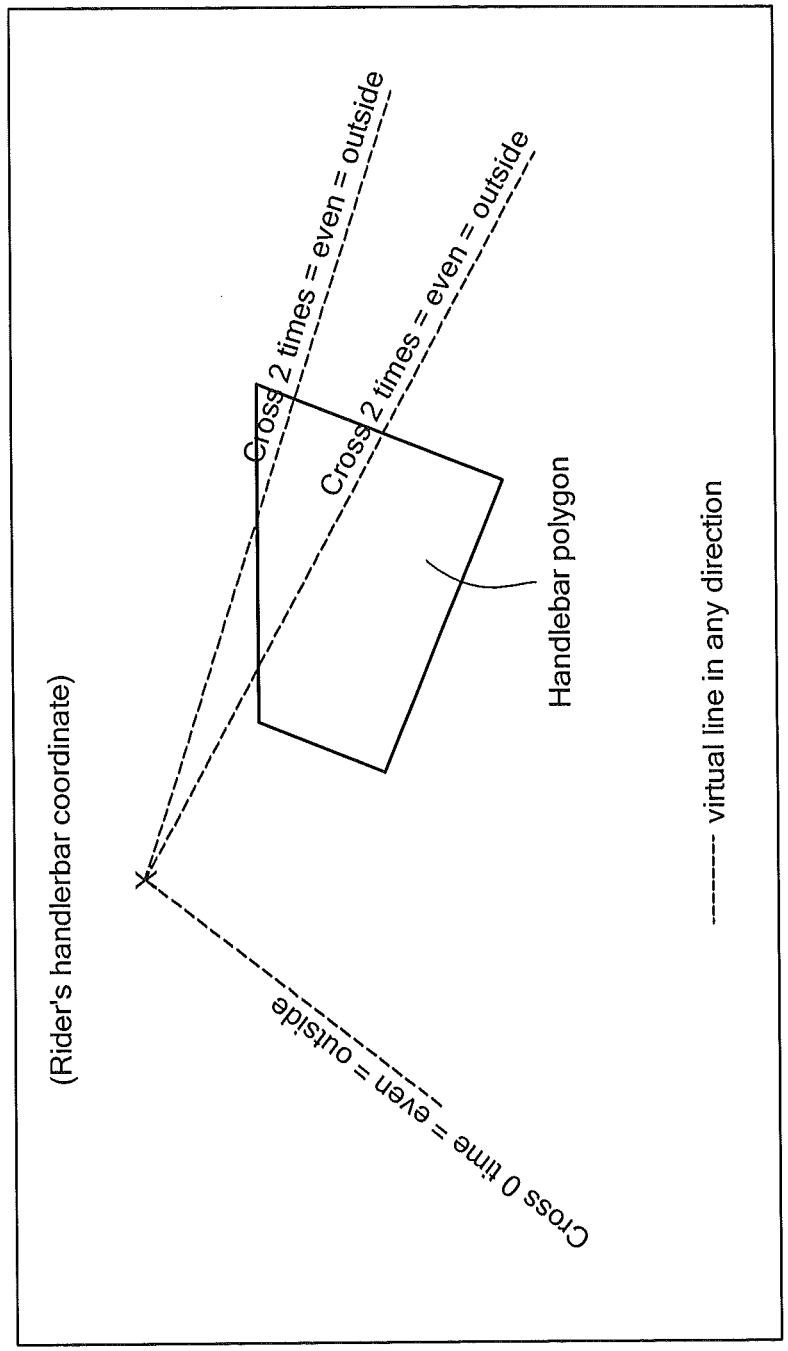
FIG. 25 depicts a graphical representation of an algorithm used to identify that a point lies outside of a polygon cloud of points, in accordance with an embodiment of the invention.
Figure 26:
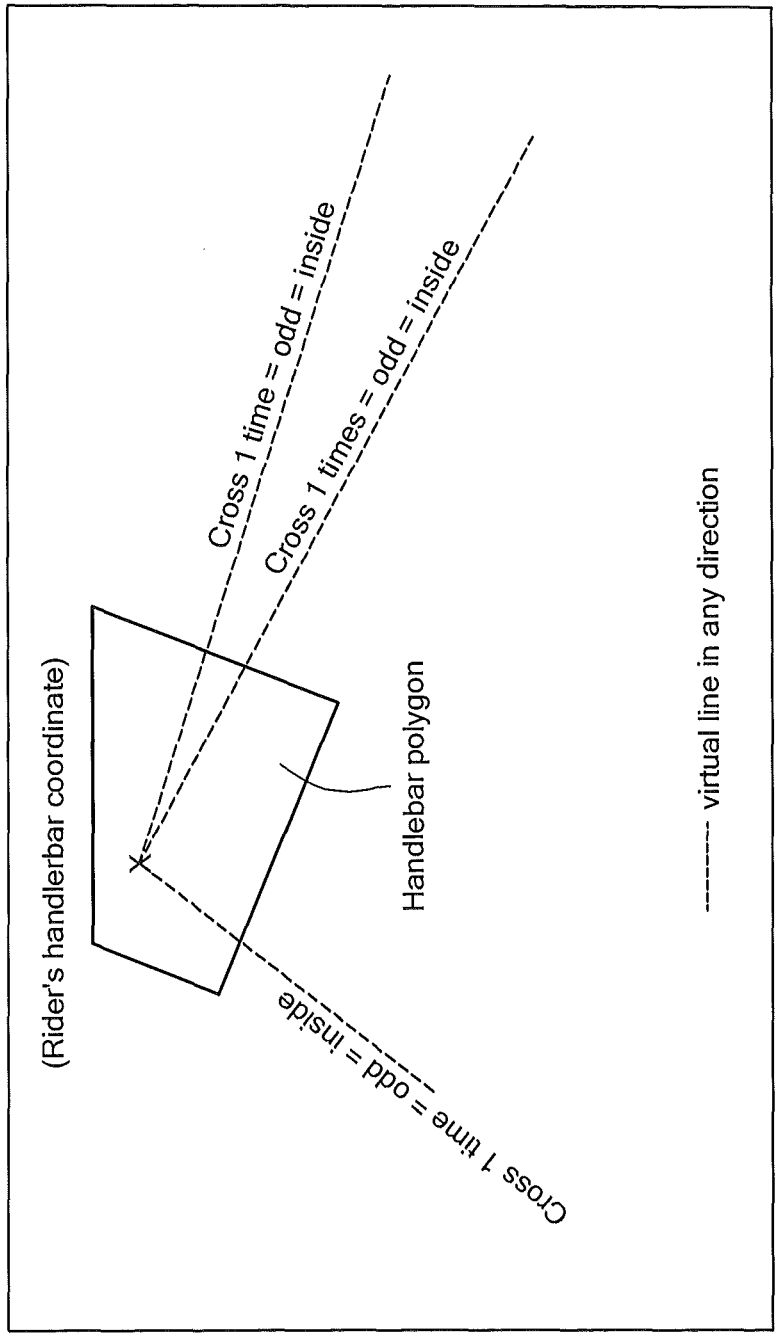
FIG. 26 depicts a graphical representation of an algorithm used to identify that a point lies inside of a polygon cloud of points, in accordance with an embodiment of the invention.

A first pass through the cloud of points will eliminate all frames that could not fit the rider's handlebar coordinate. To begin, we first check to see if the rider's handlebar X,Y coordinate is inside the different frames' handlebar polygon 230'. To find if the rider's handlebar X,Y coordinate is inside the frames' handlebar polygon, we use an algorithm that draws a virtual line in any direction from the rider's handlebar X,Y coordinate. A random number generator may be employed to select the direction of the virtual line. We then count the number of times that this virtual line crosses the frames handlebar polygon. If the count is an odd number, the algorithm concludes that the rider's handlebar X.Y coordinate is inside the polygon, if the count is an even number (including 0) the algorithm concludes that the rider's handlebar X.Y coordinate is outside the polygon. FIGS. 25 and 26 depict examples of the rider's handlebar X,Y coordinate being outside and inside the polygon, respectively. While three virtual lines are illustrated in each of FIGS. 25 and 26, only one line is required for the method described herein. Illustration of three virtual lines is merely to indicate that the virtual lines can be in any direction. The algorithm removes all frames from the list of possible candidates when the coordinates are outside the polygon.

Frames remaining from this first pass are used for a second pass. In the second pass, the algorithm applies the seat polygon to the rider's derriere coordinates in a similar manner as discussed above. After these two passes, the algorithm is capable of generating a list of frames that could possibly match the coordinates of the rider's hands and derriere. Using this list of frames, the algorithm can refine the matching stem and seat from the cloud of points that were used to create the respective polygon. Instead of applying all stems to all frames, the algorithm just applies all stems to all possible matching frames, and likewise for the seat posts.

An embodiment of the invention may be embodied in the form of computer-implemented processes and apparatuses for practicing those processes. The present invention may also be embodied in the form of a computer program product having computer program code containing instructions embodied in tangible media, such as floppy diskettes, CD-ROMs, hard drives, USB (universal serial bus) drives, or any other computer readable storage medium, such as random access memory (RAM), read only memory (ROM), erasable programmable read only memory (EPROM), electrically erasable programmable read only memory (EEPROM), or flash memory, for example, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to determine a best-fit bicycle relative to an optimal bicycle, which includes the determination of one or more of a frame, a stem, a spacer, and a seat post for the bicycle.

While the invention has been described with reference to example embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. A dynamic fit unit, comprising:
a frame;
a crankset rotatably mounted to the frame at a bottom bracket;
a handlebar adjustably disposed on the frame to be adjustable in X and Y directions relative to the crankset;
a seat adjustably disposed on the frame to be adjustable in X and Y directions relative to the crankset;
a mechanism operably connected to the handlebar and the seat to facilitate adjustment of the respective handlebar and seat in the X and Y directions;
a bicycle controller system comprising a bicycle controller responsive to computer executable code to facilitate:
movement of the handlebar and the seat in the X and Y directions;
determination of an optimal bicycle frame size for a rider based on operational characteristics provided by the rider when riding the dynamic fit unit;
determination of a best-fit bicycle frame size that is a closest match to the optimal frame size based on a comparison of available frame sizes stored in a database, the best-fit bicycle frame having a head tube and a seat tube;
determination of at least one of the optimal X,Y location of the handlebar relative to the bottom bracket based on the location of the rider's hands, and the optimal X,Y location of the seat relative to the bottom bracket based on the location of the rider's derriere;
determination of a stem and spacer from a list of available stems and spacers that will best fit between the head tube of the best-fit frame and the optimal X,Y location of the handlebar;
determination of a seat post from a list of available seat posts that will best fit between the seat tube of the best-fit frame and the optimal X,Y location of the seat; and
production of a list of the best-fit frame, the best fit stem and spacer, and the best fit seat post.

2. The unit of claim 1, wherein:
the determination of the optimal X,Y location of the handlebar relative to the bottom bracket precedes the determination of the optimal X,Y location of the seat relative to the bottom bracket.

3. The unit of claim 2, wherein:
the determination of the optimal X,Y location of the seat relative to the bottom bracket is based on a location defined by the seat tube of the best-fit frame.

4. The unit of claim 1, wherein:
the determination of the optimal X,Y location of the handlebar relative to the bottom bracket is subsequent to the determination of the optimal X,Y location of the seat relative to the bottom bracket.

5. The unit of claim 4, wherein:
the determination of the optimal X,Y location of the handlebar relative to the bottom bracket is based on a location defined by the head tube of the best-fit frame.

6. The unit of claim 1, wherein the determination of a best-fit bicycle frame size, further comprises:
using a parts list of available bicycle frames to generate a first cloud of points that relate the X,Y coordinates of the top of the head tube, and the X,Y coordinates of the top of the seat tube, relative to the bottom bracket, for each respective frame in the parts list, determine the best-fit frame that is a closest match to the optimal frame.

7. The unit of claim 1, wherein the determination of a stem and spacer from a list of available stems and spacers that will best fit between the head tube of the best-fit frame and the optimal X,Y location of the handlebar, further comprises:
using a parts list of available stems and spacers to generate a second cloud of points that relate the location of the handlebar to the location and angle of the stem post with spacer for all possible stems and spacers in the parts list, rotate and translate the second cloud of points to match the XY coordinates and angle of the top of the head tube of the best fit frame.

8. The unit of claim 7, wherein the determination of a stem and spacer from a list of available stems and spacers that will best fit between the head tube of the best-fit frame and the optimal X,Y location of the handlebar, further comprises:

from the rotated and translated second cloud of points, define a subset of the second cloud of points that will fit both the best-fit frame and the rider's hands, which defines a usable subset of stems and spacers relative to the best-fit frame.

9. The unit of claim 1, wherein the determination of a seat post from a list of available seat posts that will best fit between the seat tube of the best-fit frame and the optimal X,Y location of the seat, further comprises:
using a parts list of available seat posts to generate a third cloud of points that relate the location of the seat post top relative to the seat post bottom for all possible seat posts in the parts list, rotate and translate the third cloud of points to match the XY coordinates and angle of the top of the seat tube of the best fit frame.

10. The unit of claim 9, wherein the determination of a seat post from a list of available seat posts that will best fit between the seat tube of the best-fit frame and the optimal X,Y location of the seat, further comprises:
from the rotated and translated third cloud of points, define a subset of the third cloud of points that will fit both the best-fit frame and the rider's derriere, which defines a usable subset of seat posts relative to the best fit frame.

11. The unit of claim 1, wherein the bicycle controller system is further configured to facilitate:
determination of at least one item of riding apparel suitable for the rider based on anthropometric data relating to the rider.

12. A method for use with a dynamic fit unit, comprising:
determination of an optimal bicycle frame size for a rider based on operational characteristics provided by the rider when riding the dynamic fit unit;
determination of a best-fit bicycle frame size that is a closest match to the optimal frame size based on a comparison of available frame sizes stored in a database, the best-fit bicycle frame having a head tube and a seat tube;
determination of at least one of the optimal X,Y location of the handlebar relative to the bottom bracket based on the location of the rider's hands, and the optimal X,Y location of the seat relative to the bottom bracket based on the location of the rider's derriere;
determination of a stem and spacer from a list of available stems and spacers that will best fit between the head tube of the best-fit frame and the optimal X,Y location of the handlebar;
determination of a seat post from a list of available seat posts that will best fit between the seat tube of the best-fit frame and the optimal X,Y location of the seat; and
production of a list of the best-fit frame, the best fit stem and spacer, and the best fit seat post.

13. The method of claim 12, wherein the determination of a best-fit bicycle frame size, further comprises:
using a parts list of available bicycle frames to generate a first cloud of points that relate the X,Y coordinates of the top of the head tube, and the X,Y coordinates of the top of the seat tube, relative to the bottom bracket, for each respective frame in the parts list, determine the best-fit frame that is a closest match to the optimal frame.

14. The method of claim 12, wherein the determination of a stem and spacer from a list of available stems and spacers that will best fit between the head tube of the best-fit frame and the optimal X,Y location of the handlebar, further comprises:
using a parts list of available stems and spacers to generate a second cloud of points that relate the location of the handlebar to the location and angle of the stem post with spacer for all possible stems and spacers in the parts list, rotate and translate the second cloud of points to match the XY coordinates and angle of the top of the head tube of the best fit frame.

15. The method of claim 14, wherein the determination of a stem and spacer from a list of available stems and spacers that will best fit between the head tube of the best-fit frame and the optimal X,Y location of the handlebar, further comprises:
from the rotated and translated second cloud of points, define a subset of the second cloud of points that will fit both the best-fit frame and the rider's hands, which defines a usable subset of stems and spacers relative to the best-fit frame.

16. The method of claim 12, wherein the determination of a seat post from a list of available seat posts that will best fit between the seat tube of the best-fit frame and the optimal X,Y location of the seat, further comprises:
using a parts list of available seat posts to generate a third cloud of points that relate the location of the seat post top relative to the seat post bottom for all possible seat posts in the parts list, rotate and translate the third cloud of points to match the XY coordinates and angle of the top of the seat tube of the best fit frame.

17. The method of claim 16, wherein the determination of a seat post from a list of available seat posts that will best fit between the seat tube of the best-fit frame and the optimal X,Y location of the seat, further comprises:
from the rotated and translated third cloud of points, define a subset of the third cloud of points that will fit both the best-fit frame and the rider's derriere, which defines a usable subset of seat posts relative to the best fit frame.

18. The method of claim 12, further comprising:
determination of at least one item of riding apparel suitable for the rider based on anthropometric data relating to the rider.

* * * * *